(12) United States Patent
Vadrucci et al.

(10) Patent No.: US 7,329,807 B2
(45) Date of Patent: Feb. 12, 2008

(54) HIGH-EFFICIENCY FUSOGENIC VESICLES, METHODS OF PRODUCING THEM, AND PHARMACEUTICAL COMPOSITIONS CONTAINING THEM

(75) Inventors: Sonia Vadrucci, Zurich (CH); Joseph Brunner, Olten (CH); Rinaldo Zurbriggen, Schmitten (CH)

(73) Assignee: Pevion Biotech Ltd., Berne (CH)

( * ) Notice: Subject to any disclaimer, the term of this patent is extended or adjusted under 35 U.S.C. 154(b) by 349 days.

(21) Appl. No.: 10/719,662

(22) Filed: Nov. 21, 2003

(65) Prior Publication Data
US 2005/0064024 A1 Mar. 24, 2005

Related U.S. Application Data

(60) Provisional application No. 60/428,435, filed on Nov. 21, 2002.

(51) Int. Cl.
*A61K 9/127* (2006.01)
*C07K 14/005* (2006.01)

(52) U.S. Cl. .............. 977/799; 977/800; 977/801; 977/802; 977/803; 977/804; 977/805; 977/808; 424/450; 530/350

(58) Field of Classification Search .............. None
See application file for complete search history.

(56) References Cited

U.S. PATENT DOCUMENTS

| | | | |
|---|---|---|---|
| 4,148,876 A | | 4/1979 | Almedia et al. |
| 4,859,769 A | * | 8/1989 | Karlsson et al. .......... 514/25 |
| 5,879,685 A | | 3/1999 | Glueck et al. |
| 5,976,567 A | * | 11/1999 | Wheeler et al. .......... 424/450 |
| 6,210,708 B1 | * | 4/2001 | Walti et al. .......... 424/450 |

FOREIGN PATENT DOCUMENTS

| | | |
|---|---|---|
| WO | WO 98/52603 A | 11/1998 |
| WO | PCT/EP03/12955 | 3/2004 |
| WO | WO 2004/045582 A1 | 6/2004 |

OTHER PUBLICATIONS

Gunther-Ausborn et al (J. Virol. 74(6): 2714-2720, 2000).*
Junankar et al (Biochimica et Biophysica Acta, Biomembranes (1986), 854(2), 198-206).*
Hoekstra et al (Biochemistry 24: 4739-4745, 1985).*
Blough (J. Gen. Virol. 12(3): 317-320, 1971).*
Stegman et al (EMBO J. 6(9): 2561-2659, 1987).*
Anne M. Haywood and Bradley P. Boyer, Fusion of influenza virus membranes with liposomes at pH 7.5, Biochemistry, Proc. Natl. Acad. Sci, USA, vol. 82, pp. 4611-4615, Jul. 1985.
Harter, et. al., Hydrophobic Binding of the Ectodomain of Influenza Hemagglutinin to Membranes Occurs through the "Fusion Peptide". The Journal of Biological Chemistry, vol. 264, No. 11, pp. 6459-6464 (1989).
Eric H. Ball, Quantitiation of Proteins by Elution of Cossmassie Brilliant Blue R from Stained Bands after Sodium Dodecyl—Polyacrylamide Gel Electrophoresis. Analytical Biochemistry, vol. 155, pp. 23-27 (1986).
E. Beutler et al., The Removal of Leukocytes and Platelets from Whole Blood. J. Lab. Clin. Med, vol. 88, No. 2, pp. 328-333 (1976).
Romke Bron et al., Preparation, Properties, and Applications of Reconstitued Influenza Virus Envelopes (Virosomes). Methods in Enzymology, vol. 220, pp. 313-331 (1993).
Romke Bron et. al., Cellular Cytoplasmic Delivery of a Polypeptide Toxin by Reconstituted Influenza Virus Envelopes (Virosomes). Biochemistry, vol. 33, pp. 9110-9117 (1994).
J. Legendre et al. , Delivery of Plasmid DNA into Mammalian Cell Lines using pH-Sensitive Liposomes. Pharmaceutical Research, vol. 9, No. 10, pp. 1235-1242 (1992).
S.U. Egelhaaf, et al., New Controlled Vitrification System for Cryo-transmission Electron Microscopy: Design and Application to Surfactant Solutions. Journal of Microscopy, vol. 200, Pt2, pp. 128-139 (2000).
Walter Gerhard, The Analysis of the Monoclonal Immune Response to Influenza Virus. The Journal of Experimental Medicine, vol. 144 pp. 985-995 (1976).
Hezi Gershon et al., Mode of Formation and Structural Features of DNA-Cationic Liposome Complexes Used for Transfection. Biochemistry, vol. 32, pp. 7143-7151 (1993).
Reinhard Gluck, Adjuvant activity of immunopotentiating reconstituted influenza virosomes (IRIVs). Vaccine, vol. 17, pp. 1782-1787 (1999).
Hirt, Bernhard. Selective Extraction of Polyoma DNA from Infected Mouse Cell Cultures. J. Mol. Biol, vol. 26, pp. 365-369 (1967).
Enrico Mastrobattista et al., Targeting influenza virosomes to ovarian carcinoma cells. FEBS Letters, vol. 509, pp. 71-76 (2001).
Pierre-Alain Monnard, et al. Entrapment of Nucleic Acids in Liposomes. Biochimica et Biophysica Acta, vol. 1329, pp. 39-50 (1997).
Isabel Nunes-Correia et al., Interactions of Influenza virus with Cultured Cells: Detailed Kinetic Modeling of Binding and Endocytosis. Biochemistry, vol. 38, pp. 1095-1101 (1999).
Thomas Oberholzer, et. al. Enzymatic Reactions In Liposomes Using The Detergent-Induced Liposome Loading Method. Biochimica et Biophysica Acta, vol. 1416, pp. 57-68 (1999).
Hermann Schagger et. al., Tricine-Sodium Dodecyl Sulfate-Polyacrylamide Gel Electrophoresis for the Seperation of Proteins in the Range from 1 to 100kDA. Analytical Biochemistry, vol. 166, pp. 368-379 (1987).
Pieter Schoen, et al., Delivery of Foreign Substances to Cells Mediated By Fusion-Active Reconstituted Influenza Virus Envelopes (Virosomes). Journal of Liposome Research. vol. 3(3), pp. 767-792 (1993).
Takehiro Serikawa, et.al., A New Cationic Liposome for Efficient Gene Delivery with Serum into Cultured Human Cells: A Quantitative Analysis Using Two Independent Florescent Probes. Biochimica et Biophysica Acta, vol. 1467, pp. 419-430 (2000).

(Continued)

*Primary Examiner*—Richard Schnizer
(74) *Attorney, Agent, or Firm*—Proskauer Rose LLP

(57) ABSTRACT

The present invention relates to novel fusogenic vesicles as highly efficient and versatile encapsulation systems for delivering a substance of choice, such as nucleic acids, proteins, peptides, antigens, pharmaceutical drugs and cosmetic agents to cells and tissues.

13 Claims, 8 Drawing Sheets

OTHER PUBLICATIONS

Tong Shangguan et al., Influenza Virus-Liposome Lipid Mixing is Leaky and Largely Insensitive to the Material Properties of the Target Membrane. Biochemistry, vol. 35, pp. 4956-4965 (1996).

John J. Skehel, et. al., The Polypeptide Composition of Influenza A Viruses. Virology, vol. 44, pp. 396-408 (1971).

Theodore L. Steck et. al., Preparation of Impermeable Ghosts and Inside-out Vesicles from Human Erythrocyte Membranes. Methods Enzymol. vol. 31(Pt A), pp. 172-180 (1974).

Toon Stegmann, Membrane Fusion Mechanisms: The Influenza Hemagglutinin Paradigm and its Implications for Intracellular Fusion. Traffic. vol. 1, pp. 598-604 (2000).

Douglas K. Struck et. al., Use of Resonance Energy Transfer To Monitor Membrane Fusion. Biochemistry. vol. 20, pp. 4093-4099 (1981).

Masato Tsurudome et. al., Lipid Interactions of the Hemagglutinin HA2 NH2-terminal Segment during influenza virus-induced membrane fusion. The Journal of Biological Chemistry. vol. 267 No. 28, pp. 20225-20232 (1992).

Andreas Wagner, et.al., Enchanced Protein Loading Into Liposomes by the Multiple Crossflow Injection Technique. Journal of Liposome Research, vol. 12, No. 3 pp. 271-283 (2002).

Joseph Zabner, Cellular and Molecular Barriers to Gene Transfer by a Cationic Lipid. The Journal of Biological Chemistry, vol. 270, No. 32, pp. 18997-19007 (1995).

Rinaldo Zurbriggen, et.al., IRIV-adjuvanted Hepatitis A Vaccine: in vivo Absorption and Biophysical Characterization. Progress in Lipid Research. vol. 39, pp. 3-18 (2000).

Peter Durrer, et. al., H+-induced Membrane Insertion of Influenza Virus Hemagglutinin Involves the HA2 Amino-terminal Fusion Peptide but Not the Coiled Coil Region. The Journal of Biological Chemistry, vol. 271. No. 23 pp. 13417-13420 (1996).

Thomas Korte, et. al., Transient Changes of the Conformation of Hemagglutinin of Influenza Virus at Low pH Detected by Time-resolved Circular Dichroism Spectroscopy. Journal of Biological Chemistry vol. 272, No. 15, pp. 9764-9770 (1997).

Thomas Korte, et. al., Conformational Intermediates and Fusion Activity of Influenza Virus Hemagglutinin. Journal of Virology, vol. 73 No. 6 p. 4567-4574 (Jun. 1999).

Michael M. Kozlov, et. al., A Mechanism of Protein-Mediated Fusion: Coupling between Refolding of the Influenza Hemagglutinin and Lipid Rearrangements. Biophysical Journal. vol. 75, pp. 1384-1396 (1998).

Anu Puri, et.al., Conformational changes and fusion activity of influenza virus hemagglutinin of the H2 and H3 subtypes: effects of acid pretreatment. Journal of Virology, vol. 64, No. 8, pp. 3824-3832 (1990).

Hui Qiao, et.al., Specific Single or Double Proline Substitutions in the "Spring-loaded" Coiled-Coil Region of the Influenza Hemagglutinin Impair or Abolish Membrane Fusion Activity. The Journal of Cell Biology, vol. 141, No. 6, pp. 1335-1347 (1998).

Toon Stegmann, et.al., Effects of low pH on influenza virus. Activation and inactivation of the membrane fusion capacity of the hemagglutin. The Journal of Biological Chemistry, vol. 262, No. 36, pp. 17744-17749 (1987).

Toon Stegmann, et.al., The HA2 subunit of influenza hemagglutinin inserts into the target membrane prior to fusion. the Journal of Biological Chemistry, vol. 266, No. 27, pp. 18404-18410 (1991).

Toon Stegmann, et.al., Functional reconstitution of influenza virus envelopes, The EMBO Journal. vol. 6 No. 9 pp. 2651-2659 (1987).

Toon Stegmann, et.al., Intermediates in influenza induced membrand fusion. The EMBO Journal vol. 9 No. 13 pp. 4231-4241 (1990).

Harter, et. al., Hydrophobic Binding of the Ectodomain of Influenza Hemagglutinin to Membranes Occurs through . . . Apr. 15, vol. 264, No. 11, pp. 6459-6464, 1989, Zurich Switzerland.

Eric H. Ball, Quantitiation of Proteins by Elution of Cossmassie Brilliant Blue R from Stained Bands after Sodium Dodecyl . . . , Jul. 29, 1985, 155, 23-27, (1986); Canada.

E. Beutler et. al., The removal of leukocytes and platelets from whole blood, Aug. 15, 1975, vol. 88, No. 2, Freiburg, Germany, 1975.

Romke Bron et al., Preparation, Properties, and Applications of Reconstitued Influenza virus Envelopes (Virosomes), 1993, pp. 313-331, vol. 220Academic Press, Inc.

Romke Bron et. al., Cellular Cytoplasmic Delivery of a Polypeptide Toxin by Reconstituted Influenza virus Envelopes . . . 1994, pp. 9110-9117, vol. 33,American Chemical Society.

Jean-Yves, Delivery of Plasmid DNA into Mammalian Cell Lines using pH-Sensitive Liposomes, Jan. 27, 1992, vol. 9, No. 0, 1992, Plenum Publishing Corp.

S.U. Egelhaaf, et al., New controlled vitrification system for cryo-transmission . . . , Apr. 7, 2000, Journal of Microscopy, vol. 200, Pt2, Nov. 2000 pp. 128-139, Switzerland.

Walter Gerhard, The Analysis of the Monoclonal Immune Response to Influenza Virus, 1976, vol. 144 pp. 985-995, The Journal of Experimental Medicine, Pennsylvania.

Hezi Gershon et al., Mode of Formation and Structural Features of DNA-Cationic Liposome . . . , 1993, 32,pp. 7143-7151, The Weizmann Institute of Science, Israel.

Reinhard Gluck,Adjuvant activity of immunopotentiating reconstituted Influenza virosomes (IRIVs), Vaccine 17:1782-1787, 1999.

Bernhard Hirt, J. Mol. Biol, Selective Extraction of Polyoma DNA from Infected Mouse Cell Cultures, 1967, 26, pp. 365-369.

Enrico Mastrobattista et al., Targeting influenza virosomes to ovarian carcinoma cells, Jul. 3, 2001, pp. 71-76, Utrecht Institute for Pharmaceutical Sciences.

Pierre-Alain Monnard, et al. Entrapment of nucleic acids in liposomes, Feb. 24, 1997, pp. 39-50, Zurich Switzerland.

Isabel Nunes-Coreia et al., Biochemistry 38:1095-1101, 1999.

Thomas Oberholzer, et. al. Enzymatic reactions in liposomes using th detergent-induced liposome loading method, Biochim, Bio Days Acta vol. 1410 1999, pp. 57-68, Zurich Switzerland.

Hermann Schagger et. al., Tricine-Sodium Dodecyl Sulfate-Polyacrylamide Gel Electrophoresis for the Seperation of Proteins in the Range from . . . Anal. Biochem vol. 166 1987, pp. 368-379, Germany.

Pieter Schoen, et al., Delivery of Foreign Substances to Cella Mediated By Fusion-Active Reconstituted . . . 1993, pp. 767-792, Journal of Liposome Research, vol. 3, No. 3 The Netherlands.

Takehiro Serikawa, et.al., A new cationic liposome for efficient gene delivery with serum into cultured . . . , 2000 pp. 419-430, Dept. of Bichemistry and Cell Biology, Japan.

Tong Shangguan et al., Influenza Virus-Liposome Lipid Mixing Is Leaky and Largely Insensitive . . . , 1996, pp. 4956-4965, Dept. of Bioscience and Biotechnology, Pennsylvania.

John J. Skehel, et. al., The Polypeptide Composition of Influenza A Viruses, 1971, pp. 396-408, National Institute for Medical Research, Mill Hill, London N.W. 7. England.

Theodore L. Steck et. al., Preparation of Impermeable Ghosts and Inside-out Vesicles from Human Erythrocyte Membranes, 1970, pp. 172-181.

Toon Stegmann, Membrane Fusion Mechanisms: The Influenza Hemagglutinin Paradigm and its Implications for . . . , 2000 pp. 598-604, Munksguard International Publishers.

Douglas K. Struck et. al., Use of Resonance Energy Transfer To Monitor Membrane Fusion, 1981, pp. 4093-4099, American Chemical Society.

Masato Tsurudome et. al., Lipid Interactions of the Hemagglutinin HA2 NH2-terminal Segment . . . , 1992, vol. 267 No. 28 pp. 20225-20232, The Journal of Biological Chemistry.

Joseph Zabner, Cellular and Molecular Barriers to Gene Transfer by a Cationic Lipid, The Journal of Biological Chemistry, 1995 pp. 18997-19007 vol. 270, No. 32, Iowa City, Iowa.

Rinaldo Zurbriggen, et.al., IRIV-adjuvanted hepatitis A Vaccine: in vivo absorption and biophysical characterization, 2002, Progress in Lipid Research 39 pp. 3-18 Switzerland.

Peter Durrer, et. al., H+Induced Membrane Insertion of Incluenza Virus . . . , The Journal of Biological Chemistry, 1996, vol. 271. No. 23 pp. 13417-13427, Basel, Switzerland.

Thomas Korte, et. al., Transient Changes of the Conformation of Hemagglutinin of . . . , Journal of Biological Chemistry vol. 272, No. 15, pp. 9764-9770, 1997, Berlin Germany.

Thomas Korte, et. al., Conformational Intermediates and Fusion Activity of . . . , Journal of Virology, Jun. 1999, vol. 73 No. 6 p. 4567-4574, Bethesda, Maryland.

Michael M. Kozlov, et. al., A Mechanism of Protein-Mediated Fusion: Coupling between Refolding of . . . , Biophysical Journal vol. 75 1998 pp. 1384-1396, Bethesda, Maryland.

Anu Puri, et.al., Conformational Changes and Fusion Activity of Influenza Virus Hemagglutinin . . . , Journal of Virology, 1990 vol. 64, No. 8, pp. 3824-3832, San Francisco, CA.

Hui Qiao, et.al., Specific Single or Double Proline Substitutions in the . . . The Journal of Cell Biology, vol. 141, No. 6, 1998, pp. 1335-1347, San Francisco, CA.

Toon Stegmann, et.al., Effects of Low pH on Influenza Virus, The Journal of Biological Chemistry, 1987, vol. 262, No. 36, pp. 17744-17749, The Netherlands.

Toon Stegmann, et.al., The HA2 Subunit of Influenza Hemagglutinin Inserts into . . . , the Journal of Biological Chemistry, vol. 266, No. 27, 1991, p. 18404-18410, New Haven, CT.

Toon Stegmann, et.al., Functional reconstitution of influenza virus envelopes, The EMBO Journal vol. 6 No. 9 pp. 2651-2659, 1987, The Netherlands.

Toon Stegmann, et.al., Intermediates in influenza induced membrand fusion, The EMBO Journal vol. 9 No. 13 pp. 4231-4241, 1990, San Francisco, CA.

* cited by examiner

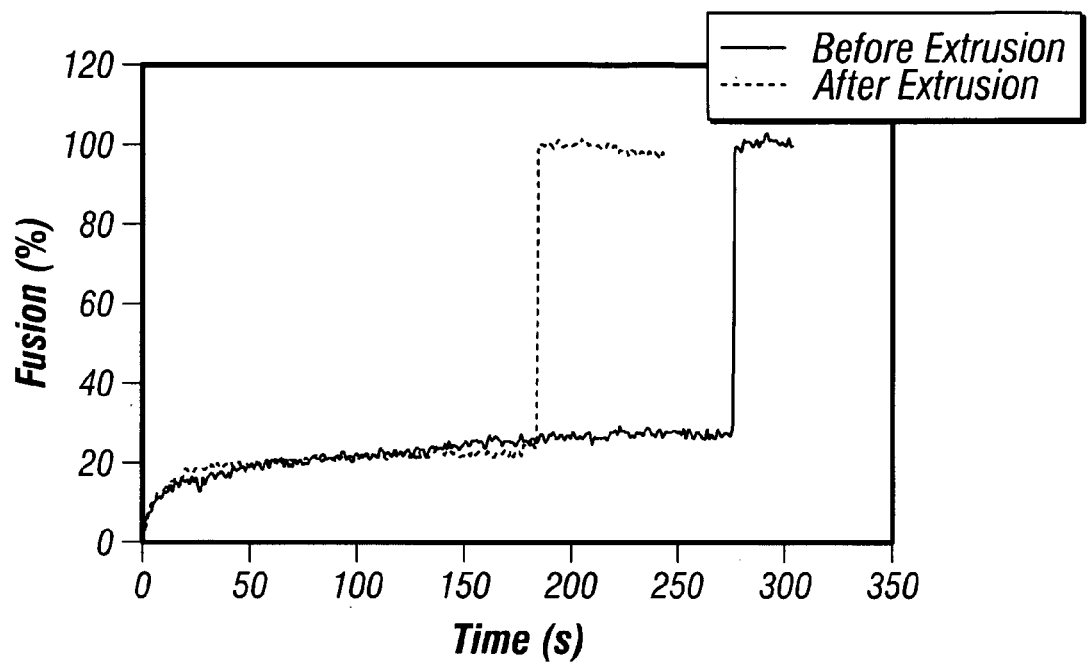
FIG. 8
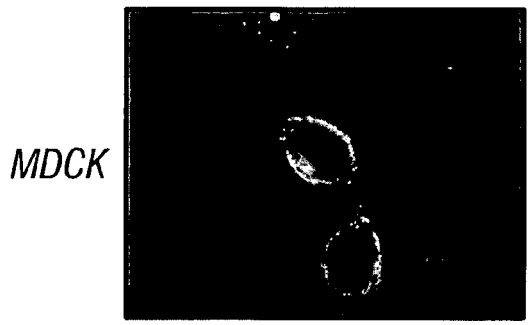
MDCK
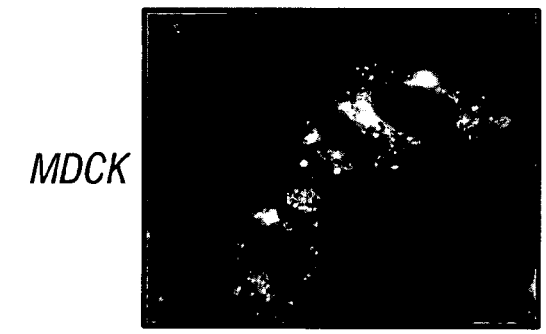
MDCK
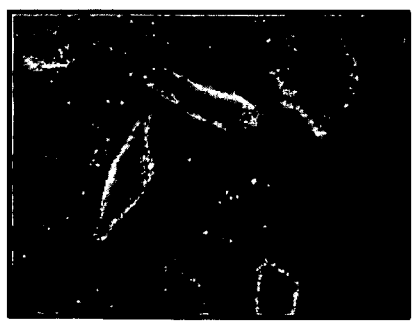
HeLa
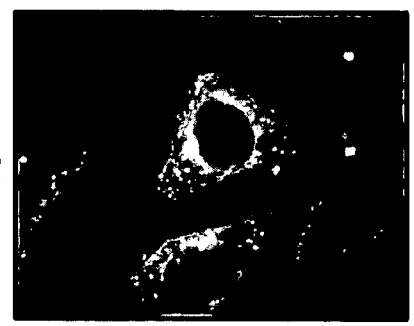
HeLa
FIG. 9A    FIG. 9B

SEQUENCE LISTING

<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: Primer for VR1012

<400> SEQUENCE: 1
gccaccagac ataatagctg                                        20

<210> SEQ ID NO 2
<211> LENGTH: 20
<212> TYPE: DNA
<213> ORGANISM: Artificial
<220> FEATURE:
<223> OTHER INFORMATION: Primer for EGFP

<400> SEQUENCE: 2
ggctgttgta gttgtactcc                                        20

<210> SEQ ID NO 3
<211> LENGTH: 15
<212> TYPE: DNA
<213> ORGANISM: Artificial
<220> FEATURE:
<223> OTHER INFORMATION: Antisense

<400> SEQUENCE: 3
aacgttgagg ggcat                                             15

```
<210> SEQ ID NO 4
<211> LENGTH: 15
<212> TYPE: DNA
<213> ORGANISM: Artificial
<220> FEATURE:
<223> OTHER INFORMATION: Scrambled

<400> SEQUENCE: 4
gaacggagac ggttt                                                    15
```

HIGH-EFFICIENCY FUSOGENIC VESICLES, METHODS OF PRODUCING THEM, AND PHARMACEUTICAL COMPOSITIONS CONTAINING THEM

CROSS-REFERENCE TO RELATED APPLICATION

This application claims the benefit of U.S. Provisional Application No. 60/428,435, filed Nov. 21, 2002, the entire contents of which are incorporated by reference herein.

FIELD OF THE INVENTION

The present invention relates to novel fusogenic vesicles as highly efficient and versatile encapsulation systems for delivering a substance of choice, such as nucleic acids, proteins, peptides, antigens, pharmaceutical drugs and cosmetic agents to cells and tissues.

BACKGROUND OF THE INVENTION

Various publications or patents are referred to in parentheses throughout this application to describe the state of the art to which the invention pertains. Each of these publications or patents is incorporated by reference herein.

One of the paramount goals of medical therapy is the efficient delivery of therapeutic substances to the site of disease. While some therapeutic substances can be delivered in free form, others require a carrier or vector in order to reach and enter their final destination, either due to their rapid clearance from the area of introduction or their inability to cross biological barriers, or due to their systemic toxicity. Delivery of substances to cells and tissues requires vectors which are efficient, flexible, easy to prepare and safe. Currently available methods for delivering substances to eukaryotic cells involve the use of either viral or non-viral vectors. Viral vectors are replication-defective viruses with part of their coding sequences replaced by that of a therapeutic gene. Although recombinant viruses are highly efficient gene delivery and expression vectors, they are currently limited to the delivery of nucleic acids and their safety profiles have not yet been established for medical use in humans.

Most non-viral delivery systems operate at the following levels: loading of the delivery vector with a substance of interest (e.g. proteins, peptides, nucleic acids, pharmaceutical or other therapeutic drugs), endocytosis, and in the case of gene delivery, nuclear targeting and entry. The major drawback of non-viral systems, such as liposomes, is their low delivery efficiency to cells (Chu et al., id.; Legendre and Szoka, 1992, Pharmaceut. Res. Vol.9, P.1235), presumably due to the absence of fusion-mediating molecules on the surface of the liposomes. A hybrid type of delivery system, the virosome, combines the efficient delivery mechanism of viruses with the versatility and safety of non-viral delivery systems. Virosomes are reconstituted envelopes without the infectious nucleocapsids and the genetic material that can be derived from a variety of viruses. These virosomes are functional, in that their membrane fusion activity closely mimics the well-defined low-pH-dependent membrane fusion activity of the intact virus, which is solely mediated by the viral fusion protein. Like viruses, virosomes are rapidly internalized by receptor-mediated endocytosis. In contrast to viral systems virosomes are safe, since the infectious nucleocapsid of the virus has been removed. Thus, virosomes represent a promising carrier system for the delivery of a wide variety of different substances, either encapsulated in their aqueous interior or co-reconstituted in their membranes. Co-reconstitution of different receptors within the virosomal membrane, furthermore, allows the targeting of virosomes to different cells or tissues. So far, virosomes are mainly used as vaccines by adding antigen onto the surface of the virosomes.

A major limitation of the protocol currently used to prepare virosomes is that it does not result in high encapsulation efficiency. At the lipid concentration at which virosomes are produced (~1 mM lipid), and given their mean diameter of approximately 200 nm, less than 1% of the aqueous phase will be entrapped within the virosomes (Schoen et al., J. Liposome Res. 3: 767-792, 1993). Such low entrapment rates reduce virosome-mediated efficiency of drug or gene delivery to cells. The development of new/novel, more efficiently loaded vesicles that retain the advantageous fusion properties of virosomes, as well as methods of making, loading, and delivering them would thus be a highly desirable goal in the field of therapeutic drug, protein and gene delivery.

BRIEF DESCRIPTION OF THE DRAWINGS

FIG. 8: This figure demonstrates the fusogenicity of the extruded vesicles resulting from the fusion of chimeric virosomes with liposomes. Remarkably, the vesicles retain their fusion activity. The proteoliposomes were extruded through nucleopore membranes. Fluorescence was recorded continuously at excitation and emission wavelengths of 465 nm and 530 nm, respectively. Measurements were carried out with a SPEX-Fluorolog-2 fluorometer equipped with a thermostated cuvette holder and a magnetic stirring device. 100% corresponded to infinite probe dilution, determined after addition of Triton X-100 (0.5% v/v). Fusion measurements were carried out at 37° C. and pH 5.0 with POPC/POPG (4:1)-LUVs containing 0.6% N-NBD-PE and N-Rh-PE.

FIG. 9: This figure shows that the proteoliposomes are rapidly internalized by cells. Rhodamine-labeled proteoliposomes are detected in MDCK and HeLa cells. Fused virosomes were bound at 4° C. for 1 h to HeLa and MDCK cells. After that, unbound material was washed away. Cells were immediately fixed (A), or incubated for another 15 min at 37° C., fixed with 3.7% (v/v) formaldehyde and analyzed by fluorescence microscopy (B).

DETAILED DESCRIPTION OF THE INVENTION

Figure 1:
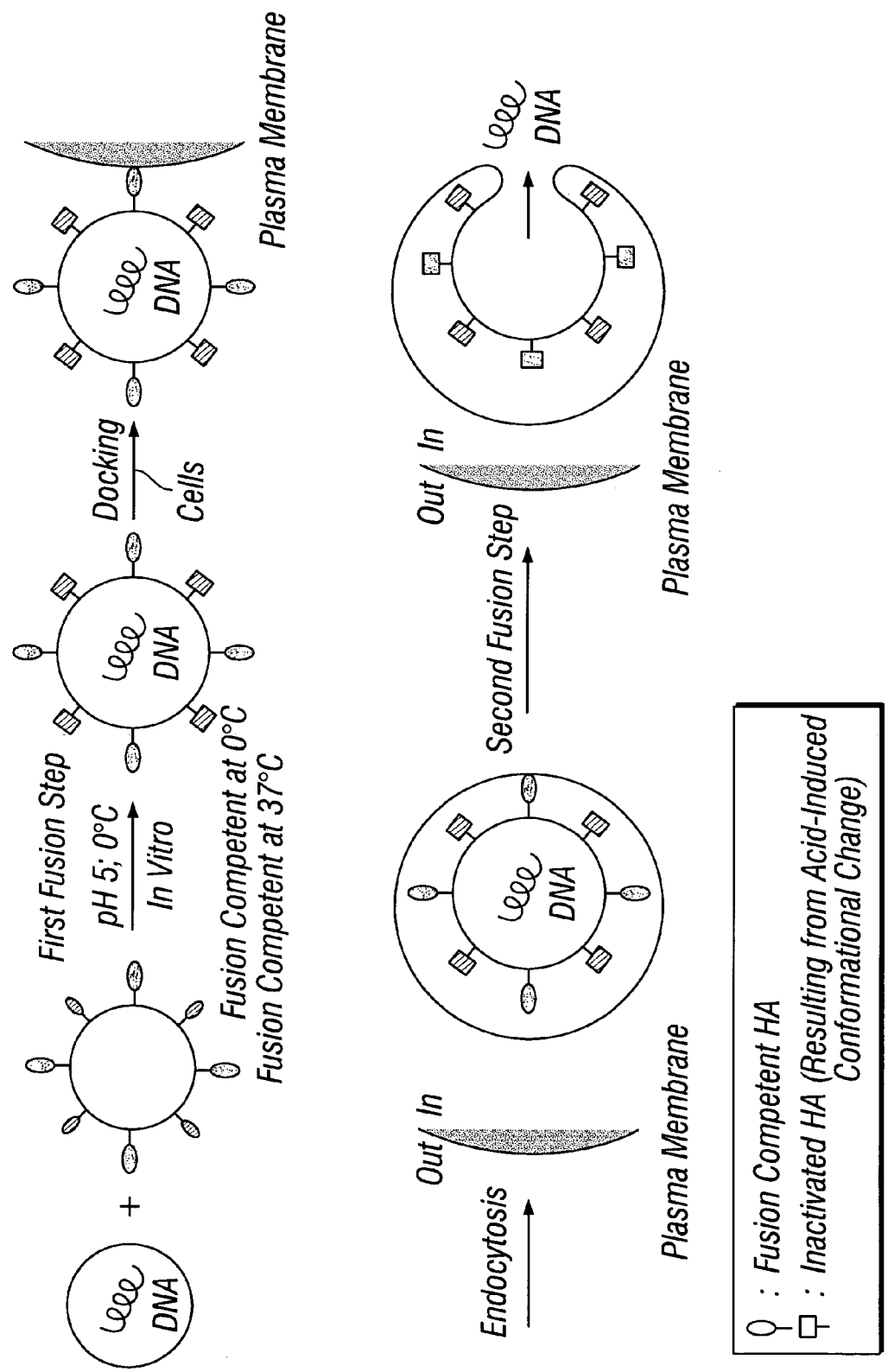
FIG. 1: This figure shows the simplified scheme representing the overall strategy of the invention. In a first fusion step, chimeric virosomes are fused at 4° C. (pH 5.0) with liposomes containing the substance to be delivered, (in this example DNA) mediated by X-31 HA. Subsequently, the resulting neutralized fusion products are incubated with cells. After receptor-mediated endocytosis, the virosome-like proteoliposomes now containing the substance to be delivered undergo a second round of fusion, triggered by the low pH within endosomes and mediated by PR8/34 HA, releasing the entrapped substance into the cytosol.

One of the problems in current virosome technology is the lack of methods for the efficient entrapment of a solute, e.g. protein, nucleic acid, or pharmaceutical drug. The present invention provides a novel approach that circumvents the problems of low virosomal entrapment efficiencies.

Therefore the invention provides a fusogenic vesicle, composed of virosomal and liposomal lipids that is capable of encapsulating at least one therapeutic or immunologically active substance whereby said fusogenic vesicle is comprised of fusion proteins, preferably at least two different fusion proteins or peptides with distinct fusion characteristics. Preferably, the vesicle is unilamellar. The vesicle has a diameter generally in the range of 100 to 600 nm, and preferably a diameter of between 100 nm and 300 nm or a diameter of between 200 nm and 400 nm, depending on the specific vesicle.

The invention takes advantage of the fact that liposomes, which can be prepared at very high lipid concentrations, have high encapsulation efficiencies. Thus, the invention provides a methodology that combines the high loading capacity of liposomes with the efficient cell-fusion and delivery of virosomes, resulting in substantially increased entrapment of solutes, like proteins, nucleic acids, and pharmaceutical drugs, within functional chimeric virosomes of controlled size that are capable of efficiently delivering therapeutic or immunologically active substances to cells.

Accordingly, in a preferred embodiment of the invention, the substance of interest is first loaded into, or encapsulated by, liposomes. The liposomal lipids which can be used in the present invention include cationic lipids, synthetic lipids, glycolipids, phospholipids cholesterol or derivatives thereof, and equivalent molecules known to those of skill in the art. Phospholipids can comprise preferably phosphatidylcholine, sphingomyelin, phosphatidylethanolamine, phosphatidylserine, phosphatidylglycerol, phosphatidic acid, cardiolipin and phosphatidylinositol with varying fatty acyl compositions. Cationic lipids can comprise preferably DOTMA (N-[(1-(2,3-dioleyloxy)propyl]-N,N,N-trimethylammonium chloride), DOTAP (N-[1-(2,3-dioleoyloxy)propyl]-N,N,N-trimethylammonium chloride, DODAC (N,N-dioleyl-N,N,-dimethylammonium chloride), DDAB (didodecyldimethy-lammonium bromide) and stearylamine or other aliphatic amines and the like. They are generally formulated as small unilamellar liposomes in a mixture with DOPE (dioleoylphosphatidyl ethanolamine) that is widely used as a 'helper' lipid to facilitate disruption of the endosomal membrane. Most preferably the liposomal lipids of the liposomes comprise POPC/DDAB.

In a second step, liposomes containing the substance of interest will be fused with chimeric virosomes having different types of fusion proteins in their membranes. The term "fusion protein" refers to peptides or proteins capable of inducing and/or promoting a fusion reaction between the fusogenic vesicle membrane and a biological membrane of the target cell. After resizing, the products of the liposome-virosome fusion will be virosome-like particles, or proteoliposomes, that contain the substance of interest in their internal cavity and are still capable of undergoing a second fusion step, under different conditions, with biological membranes in order to deliver the therapeutic or immunologically active substance.

The fusogenic vesicle of the present invention is capable of encapsulating at least one substance, preferably a therapeutic or an immunologically active substance. Examples of preferred substances suitable for encapsulation into the fusogenic vesicles are DNA, RNA, siRNA, proteins, peptides, amino acids and pharmaceutical active substances or derivatives thereof. Preferably the at least one substance is a pharmaceutical drug, an antigen, a cosmetic agent or a mixture thereof. The substance can also be a precursor to said pharmaceutical drug, antigen, or cosmetic agent that is converted into the final agent by the cell, tissue or interstitium, or by some other mechanism.

Examples of cosmetic substances are well known in the art and may comprise antipsoriatics or antifungals for dermatological use. Examples of therapeutic substances or pharmaceutical drugs are also well known in the art and may comprise anaesthetics, angiogenesis inhibitors, anti-acne preparations, anti-allergica, antibiotics, chemotherapeutics, antihistamines, antiinflammatory or antiinfective agents, antineoplastic agents, antigens, antiprotozoals, antirheumatic agents, antiviral vaccines, antiviral agents, aptoptosis inducing agents, bacterial vaccines, chemotherapeutics, cytostatica, immunosuppressive agents, laxatives, psycholeptics.

Preferred examples of cosmetic agents include tars and nystatin, while preferred examples of pharmaceutical drugs or immuno-active substances include doxorubicin, vinblastine, cisplatin, methotrexate, cyclosporine, ibuprofen, HCV-based T-cell antigens, and tumor-specific and tumor-associated antigens.

Encapsulation of the therapeutic substances, such as proteins, peptides, nucleic acids, pharmaceutical, chemotherapeutic or cosmetic drugs into liposomes can be performed by any method known in the art, including the procedures described in Monnard et al., Biochim. Biophys. Acta 1329: 39-50; 1997, in Wagner et al., J. Liposome Res., 12(3) 271-283, 2002, or in Oberholzer et al., Biochim. Biophys. Acta 1416: 57-68; 1999, among many other well-known methods. In a preferred embodiment of the invention, high liposomal encapsulation efficiencies are achieved by the freeze/thaw technique used to prepare pure lipid vesicles. With this method, approximately 50% of the initial amount of a linearized plasmid over 3 kb can be entrapped within large unilamellar vesicles (LUVs) consisting preferably of 1-palmitoyl-2-oleoyl-sn-glycero-3-phosphocholine (POPC)/didodecyldimethylammonium bromide (DDAB) (Monnard et al., Biochim. Biophys. Acta 1329: 39-50, 1997).

In one preferred embodiment, the invention provides for the preparation of virosomes containing a binary mixture of viral fusion molecules that display distinct fusion characteristics. In another preferred embodiment of the invention, different viral hemagglutinin (HA) fusion proteins are used to construct the chimeric virosomes. As shown previously (Tsurudome et al., J. Biol. Chem. 267: 20225-20232, 1992), HA fusion proteins from different strains of viruses can display markedly different temperature characteristics of fusion and inactivation. For example, at about pH 5.0, X-31 HA triggers fusion efficiently at low temperature, whereas at the same pH, HA from PR8/34 or A/Singapore virus requires elevated temperature (>25° C.). Hence, in a preferred embodiment of the invention, the chimeric virosomes contain proteins in their membrane that mediate fusion at two distinct temperatures. Different temperature-sensitivity is a particularly advantageous characteristic of the fusion proteins, as it allows convenient and simple control of fusion reactions. As an example, the present invention demonstrates that virosomes containing HA molecules from both X-31 and PR8/34 virions are capable of catalyzing two distinct fusion reactions at pH 5: the first at low temperature (0-4-10° C.), the second at elevated temperature (>25° C.). However, other fusion proteins with distinct fusion characteristics, including sensitivity to temperature, ion concentration, acidity, cell type and tissue type specificity, etc. are well known in the art and may be used for the purposes of the present invention. Fusion proteins with different fusion characteristics can be derived from different influenza strains, such as MRC-1, X-97, NIB24, NIB26, X-47, A/Johannesburg/33 and A/Singapore, to name a few.

In addition, other known viral fusion proteins may be used, such as the vesicular stomatitis virus (VSV) G protein, the Semliki forest virus (SFV) E1 protein, or the Sendai virus F protein, among many others, to construct chimeric virosomes capable of undergoing sequential and separate fusion events. Furthermore, the chimeric virosomes and resulting virosome-like proteoliposomes loaded with the therapeutic substance of interest may contain fusion proteins that target the virosome-like proteoliposomes to specific cells or tissues. Thus, for instance, fusion proteins that are specific for certain cell surface receptors, such as the gp41/gp120 protein of HIV (gp120 binds to CD4 on $CD4^+$ T lymphocytes and cells of the monocyte/macrophage lineage) can be used to target delivery of therapeutic substances to specific cell types or tissues. Other such cell- or tissue-specific fusion proteins are well known in the art and can be conveniently incorporated into the vesicles of the present invention.

In addition to the fusion proteins, the fusogenic vesicle of the present invention can further have, incorporated in the membrane or attached thereto, a cell-surface receptor, a cytokine, a growth-factor, an antibody or an antibody fragment to improve targeting of the fusogenic vesicle to different cells or tissues.

As shown by the present invention, once such chimeric virosomes are constructed, they can be fused at a first specified condition to trigger fusion of the first viral fusion protein or peptide with liposomes containing the encapsulated substance or substances of interest, such as proteins, peptides, nucleic acids, or pharmaceutical drugs. The invention demonstrates for the first time that the fusion of chimeric virosomes with substance-loaded liposomes generates virosome-like proteoliposomes which not only encapsulate the substance of interest, but are still capable of mediating an additional fusion event under different conditions, for example, under different conditions for temperature, ion concentration etc. After proper manipulation to control their size, these substance-containing proteoliposomes can be delivered to cells where they are efficiently taken up. In the environment of the endosome, the second fusion molecules can trigger a second fusion reaction between the virosomal and endosomal membranes. As illustrated in FIG. 1 this multi-step process results in the transfer of liposome-encapsulated substances into the cytosolic compartment of cells.

Figure 2:
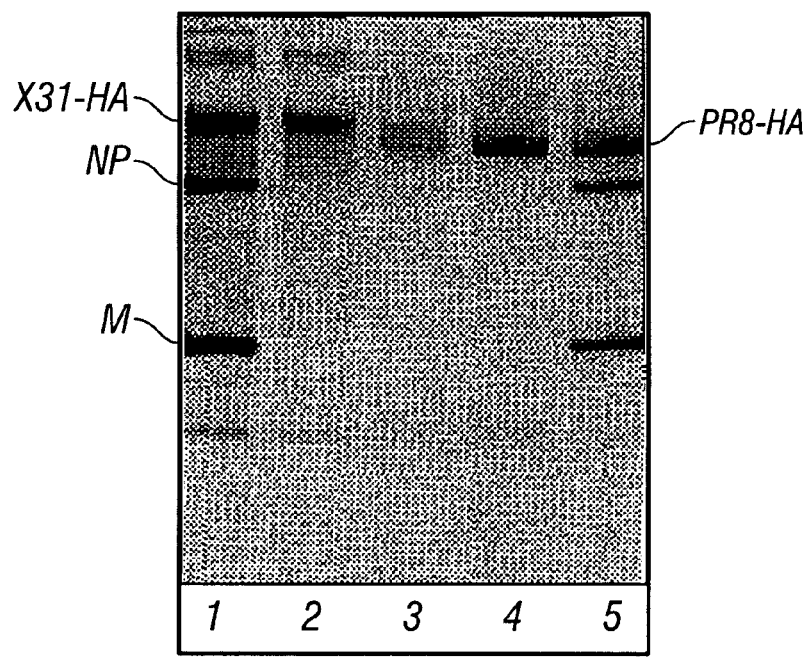
FIG. 2: This figure shows the presence of both types of fusion proteins in the membrane of the chimeric virosomes. SDS-PAGE of X-31 and PR8 virus and virosomes. Approx. 10 μg virus and 3 μg virosomes were loaded under non-reducing conditions on a SDS-Tris/Tricine 10% (v/v) polyacrylamide gel (Schägger et al., Anal. Biochem. 166: 368-379, 1987). The polyacrylamide gel was stained with Coomassie blue. Lane 1: X-31 virus. Lane 2: X-31 virosomes. Lane 3: chimeric virosomes. Lane 4: PR8 virosomes. Lane 5: PR8 virus.

Procedures for the preparation of virosomes (also referred to in this application as immunopotentiating reconstituted influenza virosomes (IRIV)) are well known to those of skill in the art (Bron et al., Methods Enzymol. 220: 313-331, 1993). Influenza virosomes, for example, can be reconstituted from the original viral membrane lipids and spike glycoproteins after solubilization of intact influenza virus with octaethyleneglycol monododecyl ether, sedimentation of the nucleocapsid (the viral glycoproteins and lipids will remain in the supernatant), and removal of the detergent in the supernatant with a hydrophobic resin (Bio-Beads SM2) (Stegmann et al., Traffic 1: 598-604, 1987). For the preparation of chimeric virosomes containing HAs from X-31 and PR8/34 strains of viruses, as one example, equal amounts of protein of both viruses were solubilized with the non-ionic detergent $C_{12}E_8$. Isolation of other viral fusion proteins is a matter of routine to those of skill in the art. After removal of the detergent with Bio-Beads SM2, new envelopes containing both types of fusion proteins were formed. SDS-PAGE of exemplary chimeric virosomes containing two different types of HA fusion proteins showed (FIG. 2) that very similar amounts of the fusion proteins, here PR8 and X-31 HA, are reconstituted into chimeric virosomes. The HA/phospholipid ratio is approximately 1.4 mg/µmol.

Figure 3:
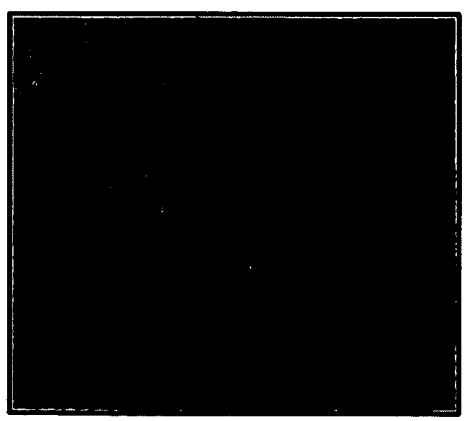
FIG. 3: This figure shows the morphology of the chimeric virosomes by cryo-TEM. They are unilamellar vesicles with diameters ranging from 150-250 nm. Scale bar 100 nm.

To determine their morphology, the chimeric virosomes constructed can be characterized by cryo-TEM. The reconstituted particles were unilamellar vesicles with a diameter ranging between 150-250 nm; some smaller vesicles were also visible (FIG. 3). The density of hemagglutinin spikes was clearly lower than that typically seen in intact virus particles. This is consistent with the measured HA/phospholipid ratio of 1.4 mg/µmol for chimeric virosomes, which is somewhat lower than that of intact virions (approximately 2 mg/µmol). Furthermore, HA-spikes are present on both sides of the membrane at about equal density.

Figures 1A, 4:
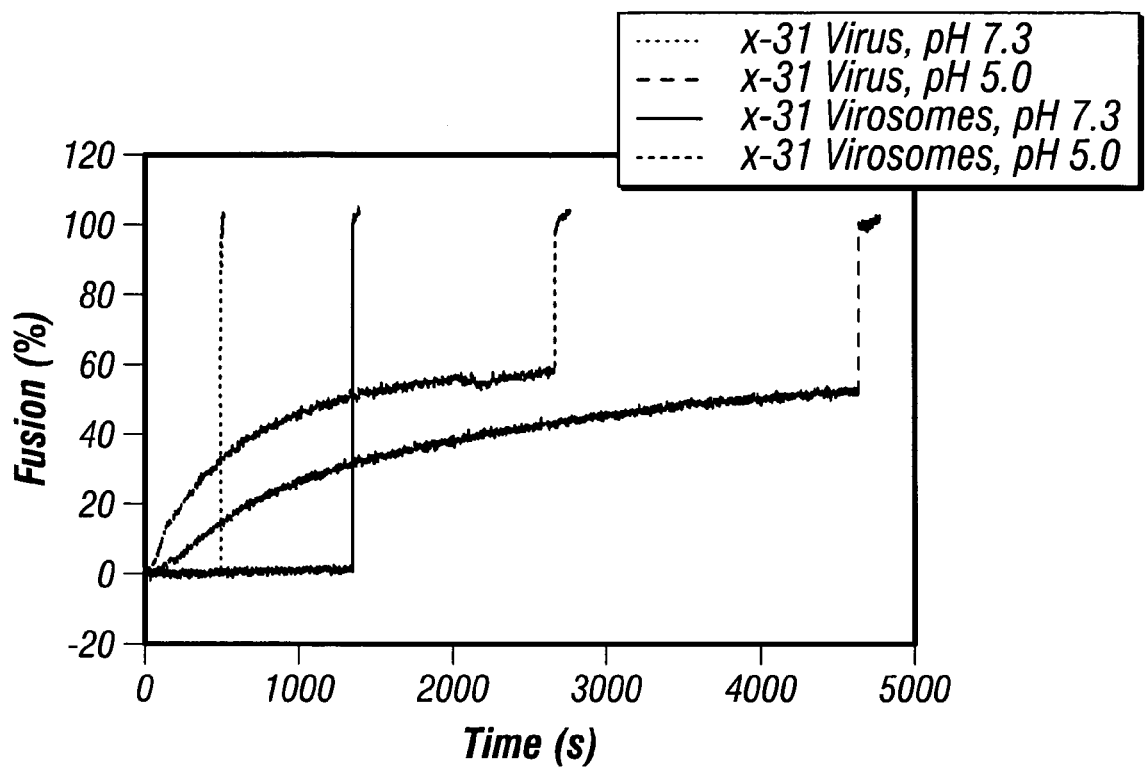
FIG. 4: This figure shows the fusion activity of X-31, PR8 viruses, virosomes and X-31/PR8 chimeric virosomes with liposomes. Fluorescence was recorded continuously at excitation and emission wavelengths of 465 nm and 530 nm, respectively. Measurements were carried out with a SPEX-Fluorolog-2 fluorometer (SPEX Industries, Inc., Edison, N.J., USA) equipped with a thermostated cuvette holder and a magnetic stirring device. For calibration of the fluorescence scale the initial residual fluorescence of the liposomes was set to zero and the fluorescence at infinite probe dilution to 100%. The latter value was determined by addition of Triton X-100 (0.5% v/v). 1) X-31 virus and virosomes fused with POPC/POPG-LUVs. 2) PR8/34 virus and virosomes incubated with POPC/POPG-LUVs. 3) Chimeric virosomes incubated with POPC/POPG-LUVs. a) fusion measurements at 4° C.; b) Virus and virosomes were incubated at 4° C. and pH 5.0 for 1 h with POPC/DDAB-LUVs before fusion measurements at 37° C.
Figures 1B, 4:
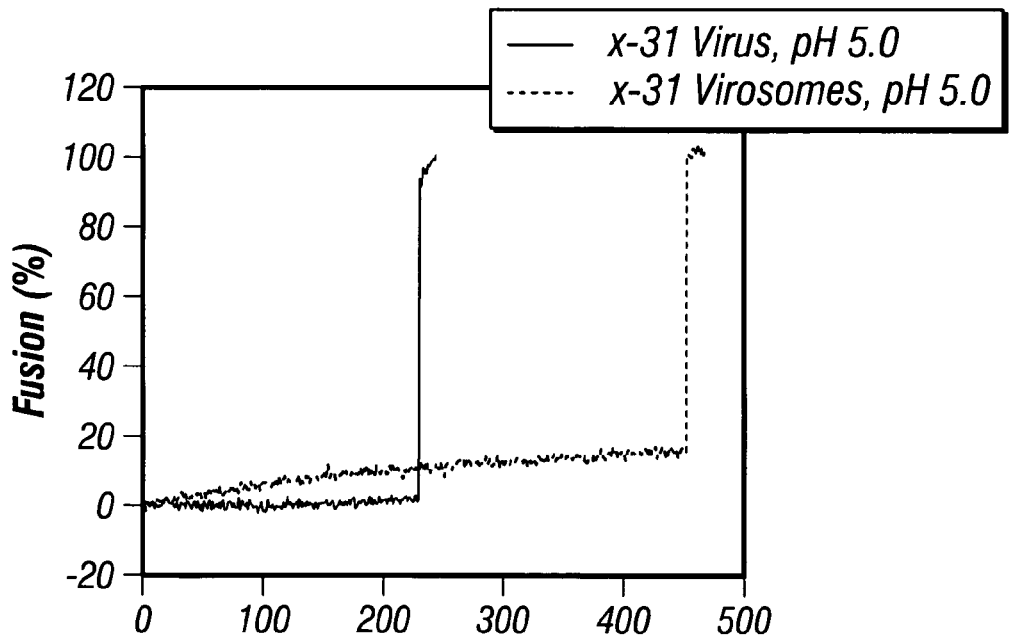
Figures 2A, 4:
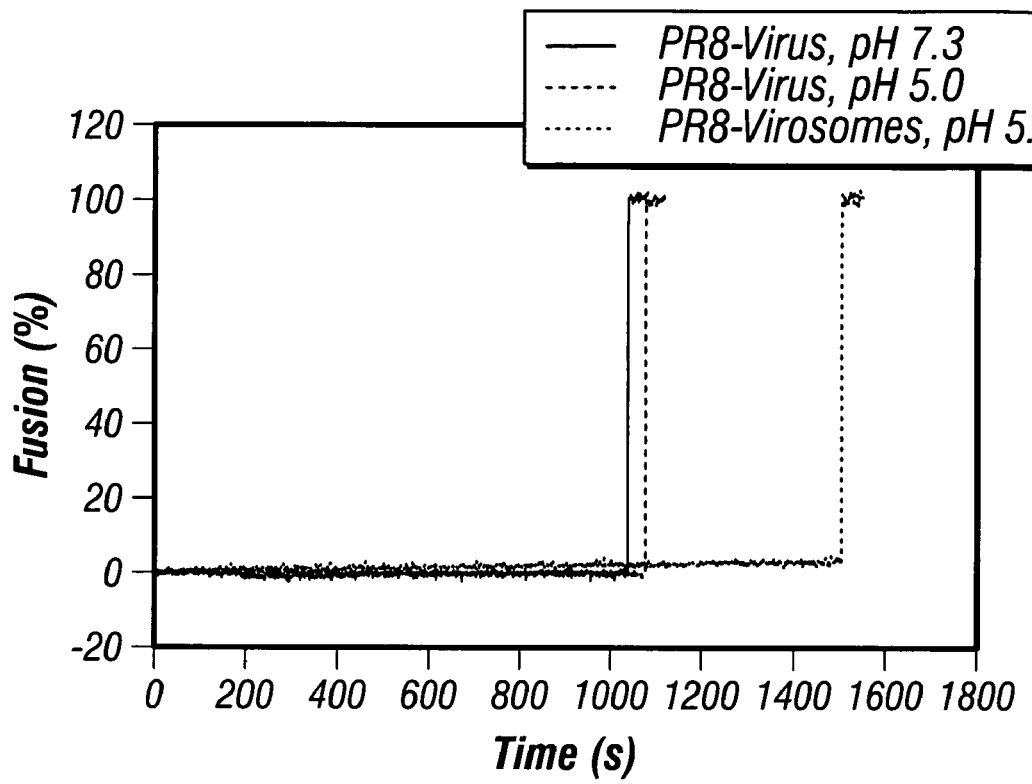
Figures 2B, 4:
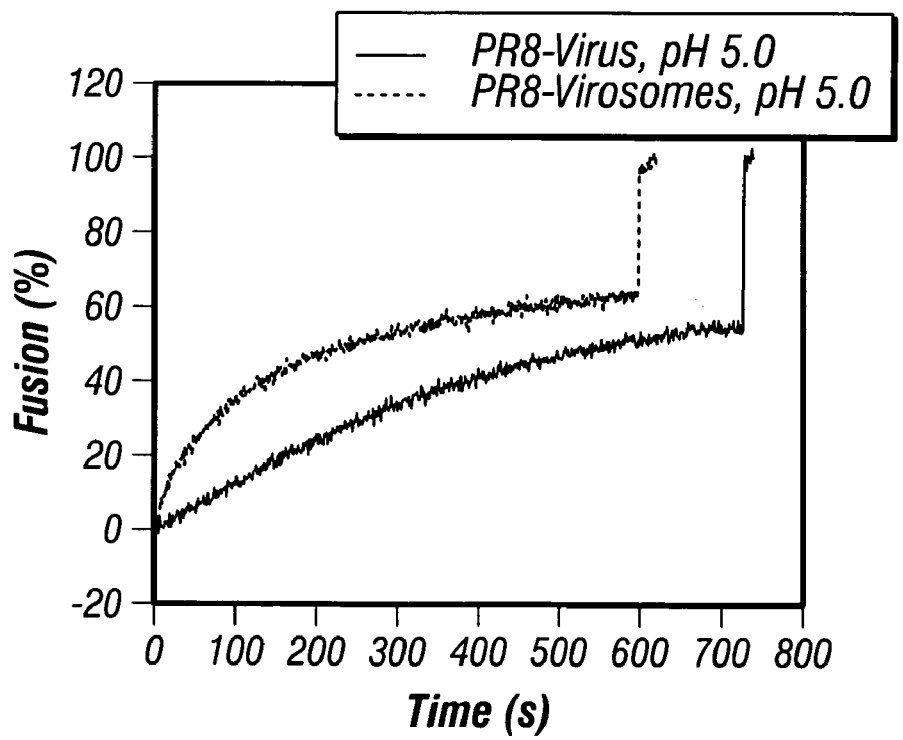
Figures 3A, 4:
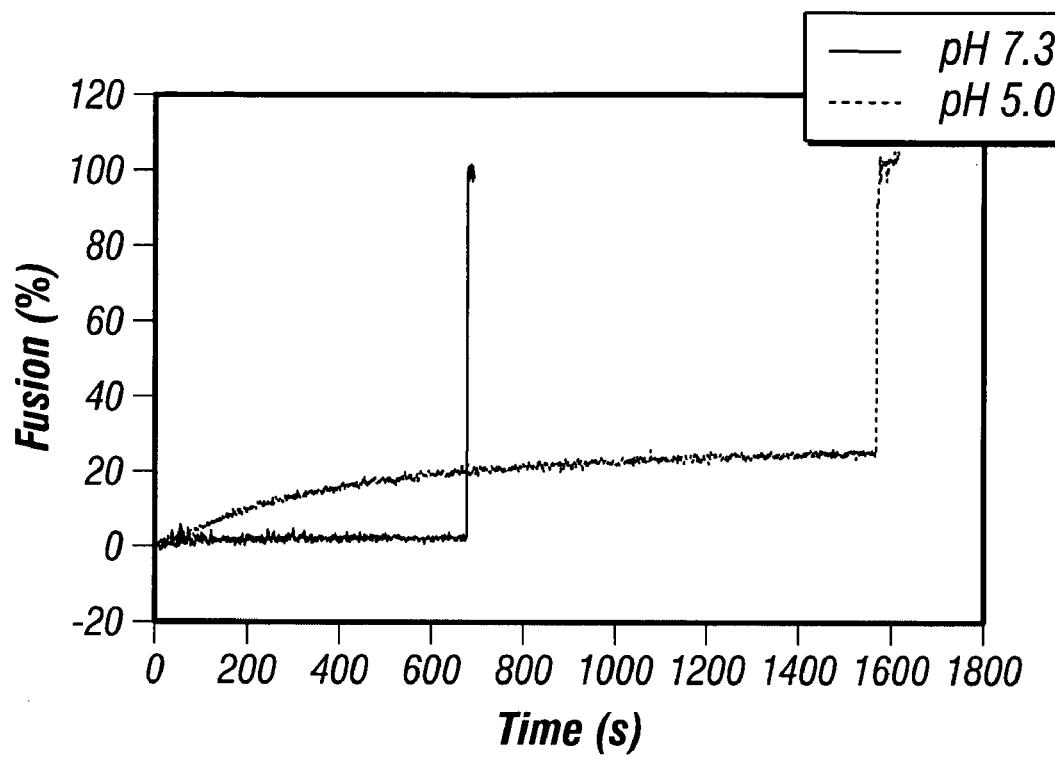
Figures 3B, 4:
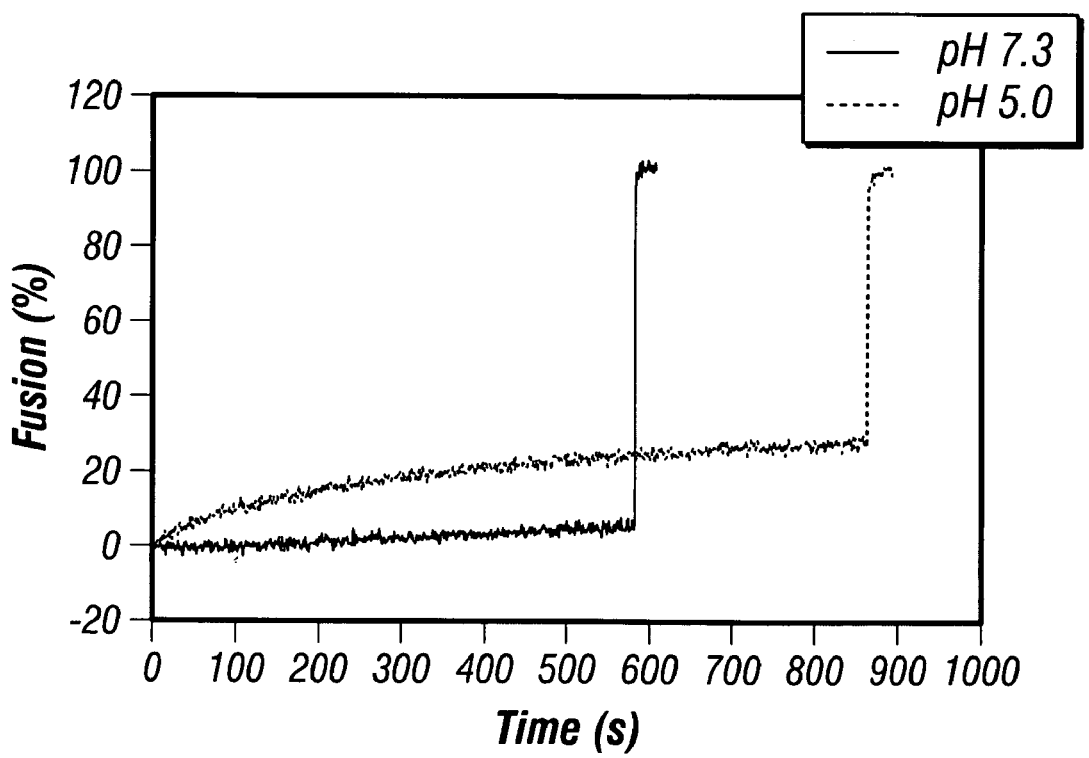

The fusion properties of chimeric virosomes with liposomes, such as the dependence of fusion activity on a certain temperature, pH, or other parameter, in vitro can be determined using the lipid mixing assay (Struck et al., Biochemistry 20: 4093-4099, 1981). This assay is based on fluorescence resonance energy transfer (FRET) and makes use of the two fluorophores N-NBD-PE (energy-donor) and N-Rh-PE (energy-acceptor) present within one of the two membranes (e.g. liposomes). A variant of this assay, utilizing the same donor N-NBD-PE but a different acceptor, cholesterol-anthracene-9-carboxylate (CAC), may also be used. Another variant of this assay, utilizing the same acceptor N-Rh-PE but a different donor, Bodipy 530/550-DHPE, may also be used. Upon fusion the two fluorophores move apart and the fluorescence emitted by the donor increases (or that of the acceptor decreases). As an example, the fusion activity of X-31/PR8/34 chimeric virosomes was compared with that of X-31 and PR8/34 virus as well as with the corresponding virosomes (FIG. 4). As target membranes, unilamellar liposomes prepared from POPC/POPG (4:1) and the two fluorophores (0.6% each) were used. As shown in FIG. 4.1$a$, both X-31 virus and X-31 virosomes fused efficiently with the liposomes at 4° C. and pH 5.0. Because the X-31 and PR8/34 HA fusion proteins both require an acidic pH, no fusion occurred at neutral pH. Preincubation of X-31-HA at low temperature and low pH almost completely abolished its fusion-activity (FIG. 4.1$b$).

By contrast, at 4° C., pH 5.0, PR8/34 virus and virosomes neither fused nor, importantly, underwent inactivation (FIG. 4.2$a$). However, they were able to trigger fusion at 37° C. (FIG. 4.2$b$). According to these data, chimeric virosomes can be designed to perform two distinct fusion reactions, depending on the parameters for which each fusion protein is specific. For example, the PR8/34/X-31 chimeric virosomes can perform one fusion reaction at low temperature (4° C.; FIG. 4.3$a$) and a second fusion reaction at higher temperature (37° C.; FIG. 4.3$b$). A surprising and important discovery of the present invention is that the preincubation of chimeric virosomes with target membranes at low temperature and low pH does not eliminate fusion-activity at elevated temperature (FIG. 4.3$b$). Therefore, the present invention provides for a controlled fusion reaction that results in the formation of loaded virosomes capable of fusing again under different conditions.

Figure 6:
FIG. 6: This figure shows the morphology of loaded liposomes by cryo-TEM of. They are unilamellar and measure between 100-150 nm in diameter. Scale bar 100 nm.

The fact that the prepared liposomes are unilamellar is of great importance for the subsequent fusion step with chimeric virosomes, since the loaded substance should be released into the internal cavity of the newly formed vesicle rather than remaining trapped between membrane layers. To examine a possible interaction of the loaded substance with the lipids used and its effect on the liposome morphology, plasmid-containing vesicles were subjected to cryo-TEM. The electron micrographs in FIG. 6 show that the cationic vesicles were unilamellar and 100-150 nm in size. In contrast to other preparations containing cationic lipids and DNA, where multilamellar, tubular structures are formed (Gershon et al., Biochemistry 32: 7143-7151, 1993), advantageously in this procedure homogeneous unilamellar vesicles are generated.

Figure 5:
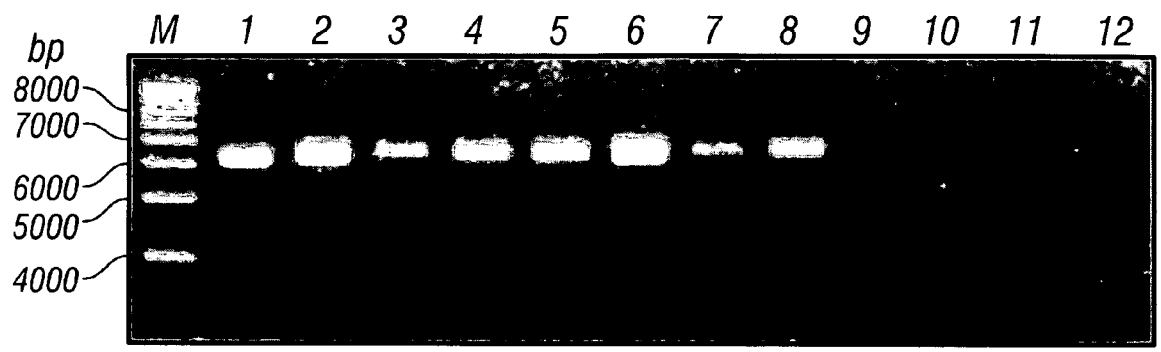
FIG. 5: This figure shows the encapsulation efficiency of DNA into POPC/DDAB-liposomes. DNA-containing liposomes were prepared by the freeze/thaw method as described in the examples and digested for 3 h at 37° C. with DNase I/Exonuclease III. After that, encapsulated DNA was phenol/chloroform extracted and subjected to gel electrophoresis on a 1% agarose gel. In lane M 1 Kb plus Ladder marker was loaded. As control 100 ng (lane 1) and 200 ng plasmid-DNA (lane 2) were directly loaded on the gel. As another control untreated (not DNase I digested) DNA-liposomes corresponding to 20 ng (lane 3), 50 ng (lane 4), 100 ng (lane 5) and 200 ng (lane 6) plasmid were phenol/chloroform extracted. The aqueous phase was loaded on the gel. DNase I digested liposomes corresponding to an initial DNA-amount of 50 ng (lane 7) and 100 ng (lane 8) were treated like the samples before. Lane 9 and 10 correspond to the same amount of liposomes, except that liposomes had been solubilized with 1% (v/v) Triton X-100 before DNase I treatment. In lane 11 and 12 DNA was not encapsulated, but added to empty liposomes. Also these liposomes were treated as described above.
Figure 7A:
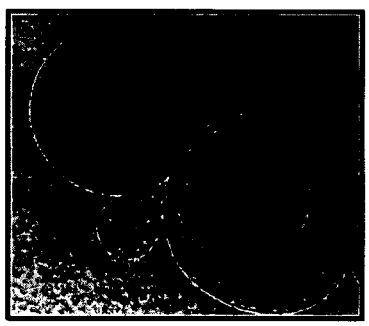
FIG. 7: This figure shows the products of the fusion between the chimeric virosomes and the loaded liposomes by cryo-TEM before (upper panels) and after extrusion (lower panels). Before extrusion, the vesicles are of widely varying sizes with some vesicles exceeding 900 nm. This result indicates multiple rounds of fusion. Scale bars upper panels: 500 nm; scale bars lower panels: left: 100 nm; right: 200 nm.
Figure 7B:
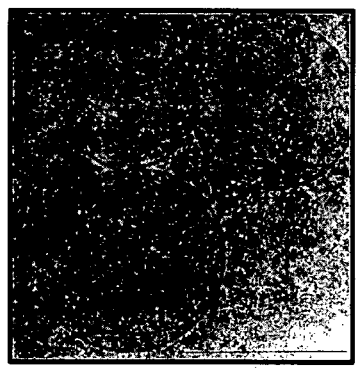
Figure 7C:
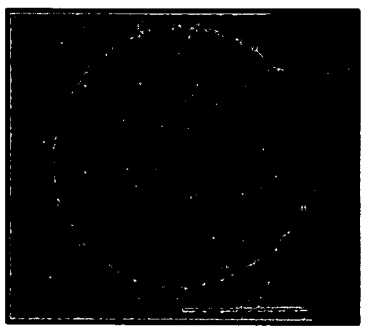
Figure 7D:
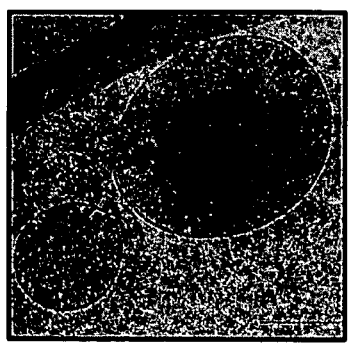

To demonstrate the feasibility of the approach, the encapsulation efficiency of the therapeutic or immunologically active substance of choice, in this case the 6.5 kb model plasmid, was determined. As determined after digestion of free plasmid DNA with DNase I/Exonuclease III digestion and separation by gel filtration the entrapment efficiency achieved was approximately 40% of a circular, 6.5 kb model plasmid. Quantitation of the remaining intact DNA can either be based on radioisotopic labeling of the DNA, or visual comparison with standard amounts on an agarose gel following staining with ethidium bromide, as described in FIG. 5. To ascertain that accessible DNA was degraded quantitatively, control experiments were performed in which all DNA was accessible (i.e. liposomes solubilized with a detergent (FIG. 5, lanes 9 and 10) or DNA on the outside (FIG. 5, lanes 11 and 12)). These results thus demonstrate that the DNase I/exonuclease III-resistant fraction is effectively entrapped in the internal cavity of the liposomes, and not just inaccessible to DNase I and exonuclease III because of (protective) interactions with the cationic lipid. The entrapment achieved (35-40%) is quite significant, thus making this approach suitable for therapeutic applications.

Following the successful preparation of the chimeric virosomes and the unilamellar liposomes loaded with the substance of interest, the present invention provides for the fusion of these two vesicular systems. However, there are several major obstacles that had to be overcome before the desired fusogenic and loaded virosomes were obtained. Because virosomes are capable of fusing both with liposomes and other virosomes, as well as with the primary products of fusion, multiple rounds of fusion were shown to occur in the mixture of loaded liposomes with chimeric virosomes. These uncontrolled fusion events resulted in a significant percentage of large, undefined structures. Such large structures are unsuitable for the delivery of therapeutic substances to cells, as their endocytosis by cells is expected to be severely compromised. Furthermore, the multiple rounds of fusion resulted in populations of virosome-like end products (proteoliposomes) with a wide variety of different sizes. Such heterogeneously sized populations are therapeutically undesirable because the amount and dosage of the encapsulated therapeutic substance cannot be controlled. In addition, encapsulation of the original liposome-entrapped therapeutic or immunologically active substance of interest within an internal compartment of the resulting chimeric virosome-like proteoliposomes has not previously been demonstrated. It was doubtful whether successful encapsulation would be achieved or whether fusion would result in partial or total release of the therapeutic substance of interest. Lastly, it was uncertain whether the fused vesicles would retain fusion capacity under the second set of conditions or parameters, such as elevated temperature.

To investigate the products of the fusion between liposomes and virosomes containing different fusion proteins, samples of fused vesicles were characterized by cryo-transmission electron microscopy (cryo-TEM). The liposome-virosome fusion products showed vesicles with a size distribution between 450 nm and 900 nm (FIG. 7, upper panels). Some smaller vesicles, possibly original virosomes, were detected (FIG. 7, top left). On the other hand, it appeared that all of the liposomes underwent at least one round of fusion. The presence of very large vesicles (>900 nm) is evidence that multiple rounds of fusion take place in the virosome-liposome fusion step. In order to solve the problem of uncontrollable fusion and to generate homogeneously sized vesicles that would allow control over drug or substance delivery dosage, the vesicles would have to be manipulated so as to generate vesicles of uniform size. Ideally, the large diameter vesicles that are unsuitable for endocytosis would have to be reduced in size without causing loss of the encapsulated contents or fusogenicity. Therefore, the present invention further comprises re-sizing the fusogenic vesicles obtained after fusing liposomes encapsulating at least one therapeutic or immunologically active substance with virosomes having fusion proteins with distinct fusion characteristics. In accordance with the invention, said resizing can be carried out by extrusion of the vesicles.

Accordingly, the present invention provides for a size-reduction step of the virosome-like proteosomes obtained through the fusion of chimeric virosomes with loaded liposomes, which remarkably causes neither loss of the encapsulated substance from the vesicles nor inactivation of the remaining functional fusion protein with concomitant loss of fusogenicity. Thus, in a preferred embodiment of the invention, the reaction products of the virosome-liposome fusion reaction are subjected to a nucleopore extrusion step in order to reduce their size. As shown in FIG. 7, lower panels, extrusion through 200 nm pores yields vesicles of approximately half of the original size as shown by cryo-TEM. Most particles are between 100-300 nm, rarely also larger vesicles (500-600 nm) can be detected. The fact that the extrusion step results in re-sized fusogenic virosome-like vesicles without significant loss of encapsulated substance is a rather unexpected and highly advantageous result, as the shearing forces applied during extrusion would be expected to rupture the majority of the membranes, causing loss of entrapped material and inactivation of the fusion proteins. That the extrusion step leads neither to any significant loss of the entrapped plasmid-DNA nor inactivation of the second fusion protein (the PR8-hemagglutinin), was verified by testing the fusogenicity and the DNA-content of extruded proteoliposomes. FRET-measurements showed that the fusogenicity of the loaded proteoliposomes before and after extrusion was the same (FIG. 8).

Further, the plasmid content of the extruded proteoliposomes was determined. Toward this end, liposomes containing radioactive plasmid DNA were prepared (free DNA was digested with DNAse and nucleotides were removed by gel filtration; entrapped DNA=100%). Subsequently, these liposomes were subjected to fusion with virosomes. One aliquot of the fusion products was treated directly with DNase I, the other following extrusion through nucleopore membranes. After removal of the free nucleotides, the radioactivity entrapped within the proteoliposomes was determined. From the results it can be concluded that during the initial fusion step, no more than 15% (±5% s.d.; n=2) and during both the fusion and extrusion step, no more than 25% (±3% s.d.; n=2) of the originally entrapped DNA is lost. Thus, the amount of radioactivity found in proteoliposomes after extrusion is only slightly lower than before extrusion. That the liposome-virosome fusion retains most of the entrapped substance is even more surprising when one considers the reports that HA-mediated membrane fusion is a leaky process (Shangguan et al., Biochemistry 35: 4956-4965, 1996).

Thus, the present invention provides a procedure for the preparation of fusion-competent proteoliposome vesicles that efficiently encapsulate a substance of interest for delivery to cells and tissues. The cellular uptake of these novel proteoliposome vesicles can be traced by the fluorescent lipid rhodamine phosphatidylethanolamine (Rh-PE) stably inserted within the membrane bilayer. The labeled proteoliposomes were added to MDCK or HeLa-cells (approx. $1 \times 10^5$ cells) cultured on cover slips in 24-well plates. Following incubation at 4° C. for 1 h to allow binding to cells, unbound particles were removed and cells were incubated for an additional 15 min at 37° C. After fixation with formaldehyde cells were analyzed by fluorescence microscopy.

After this (short) incubation at 37° C., a clear punctate, perinuclear staining was visible (FIG. 9B), indicating that rhodamine-labeled proteoliposomes had been rapidly internalized. This process was temperature dependent since at 4° C. all particles remained at the cell surface (FIG. 9A). Furthermore, it was also dependent on the fusion protein in the vesicle membrane, as protein-free Rh liposomes were not internalized to a detectable extent within 2 hours. These results show that chimeric proteoliposomes are rapidly internalized; in all likelihood by receptor-mediated endocytosis, as is the case for influenza virus. Likewise, dextran can be added to liposomes at a high concentration and because of its smaller size it is assumed that several labeled molecules can be incorporated into one proteoliposome. In fact, theoretically, at the concentration of dextran used (37.5 mg/ml) approximately 170 dextran molecules can be incorporated into one liposome. With the degree of substitution being six fluorophores per dextran molecule, one thousand Texas-red molecules should be available per liposome.

Figure 10A:
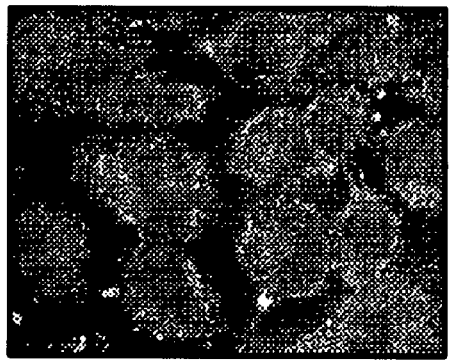
FIG. 10: This figure shows the rapid uptake of proteoliposomes loaded with Texas Red dextran by HeLa cells. HeLa cells were incubated with Texas Red dextran-containing proteoliposomes for 1 h at 4° C. After that, unbound material was washed away and fixed with 3.7% (v/v) formaldehyde (A). Otherwise, cells were further incubated for 15 min (B), 2 h (C) or 5 h (D) at 37° C. After fixation, cells were analyzed by fluorescence microscopy. Objective magnification: for (A) 63×; for (B), (C), (D) 100×.
Figure 10B:
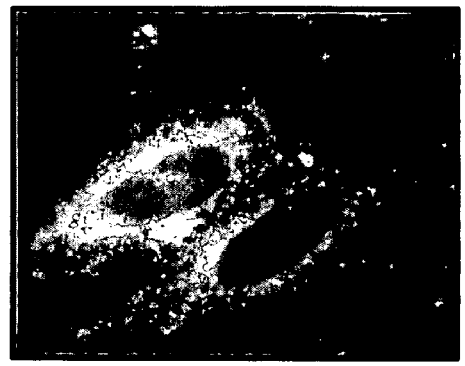
Figure 10C:
Figure 10D:
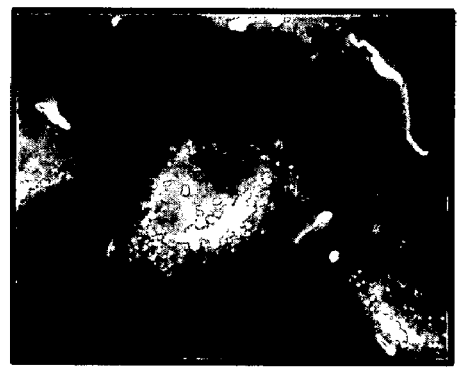

It was expected that if the encapsulated material is released into the cytosol a diffuse, cytosolic staining should be visible by fluorescence microscopy versus a punctate perinuclear staining if the substance remains entrapped. Dextran was entrapped into POPC/DDAB-liposomes as described in the examples. Liposomes were fused with chimeric virosomes and the fusion products added to cells cultured on coverslips. Cells were incubated for 1 h at 4° C., then unbound material was washed away and cells were incubated for different time at 37° C. After fixation with 3.7% (v/v) formaldehyde, cells were analyzed by fluorescence microscopy. Uptake of dextran-proteoliposomes could be detected after a 15 minute incubation at 37° C., as already seen for rhodamine-labeled proteoliposomes. At this stage a substantial amount of dye was at the cell surface (FIG. 10B). Later (FIGS. 10C and D) a more perinuclear staining could be observed.

To further demonstrate the feasibility of the approach, the encapsulation efficiencies of other therapeutic substances of choice were determined. Hydrophobic as well as hydrophilic peptides, proteins (e.g. recombinant green fluorescent protein, GFP) and small molecules (e.g. PicoGreen) were used. Table 1 represents a summary of these results. With the conventional preparation procedure (Schoen et al., J. Liposome Res. 3: 767-792, 1993) encapsulation efficiencies below 5% were obtained. However, the new approach resulted in encapsulation efficiencies at least above 15% in every case (Table 1).

TABLE 1

Encapsulation efficiencies of different molecules at subsequent steps during IRIV preparation

| Encapsulated molecule | Liposomes (0.2 μm diameter)[1] | "Fused" IRIV[2] (Proteoliposomes) | "Conventional" IRIV[3] |
|---|---|---|---|
| Hydrophilic peptides | >20% | >18% | 0.1-0.5% |
| Hydrophobic peptides | >15% | >15% | 0.1-2.0% |
| GFP[4] | >15% | >15% | 0.1-0.5% |
| PicoGreen[5] | >30% | >25% | 0.5-4.5% |
| Plasmid DNA | >30% | >25% | 0.1-1.0% |

[1,2]Preparation of liposomes and liposomes fused with IRIV (proteoliposomes) is described in detail in Example 6
[3]Preparation of "conventional" IRIV is described in Example 3
[4]GFP: green fluorescent protein
[5]PicoGreen: DNA intercalator Thus, the present invention provides for improved, virosome-based carrier systems for the delivery of therapeutic substances, including macromolecules, to cells. Because of their safety profile (when compared to viral vectors) and their rapid cellular uptake the virosome-like fusogenic proteoliposomes of the instant invention represent a promising system that can also be used for the preparation of a pharmaceutical formulation for the treatment or prevention of viral, bacterial and fungal infections, degenerative diseases, hyper-proliferative diseases and other disorders including cancer, infectious diseases, chronic infectious diseases, chronic diseases, allergies, cardiovascular diseases, inflammatory diseases (including skin inflammatory diseases such as psoriasis), immune diseases, cancer immune disorders, asthma or arthritis.

A further advantage of the vesicles presented here is their potential targeting to specific cells or tissues by co-reconstituting receptors, antibodies, or antibody fragments (Mastrobattista et al., FEBS Lett. 509: 71-76, 2001) within the vesicle membrane. In addition, because virosomes have been shown to work as excellent adjuvants (Glück, Vaccine 17: 1782-1787, 1999), the virosome-like proteoliposomes of the present invention can be adapted for use in vaccination, in addition to drug delivery. By providing efficient encapsulation of substances, including macromolecules, the present invention fulfills an urgent need in the art. The 25-30% entrapment efficiencies shown here of a model plasmid within closed, unilamellar fusogenic proteoliposomes far exceed those of previously used techniques in which entrapment efficiencies below 1% were measured (Schoen et al., J. Liposome Res. 3: 767-792, 1993). In addition, the prepared exemplary proteoliposomes were found to undergo efficient fusion with model membranes at low pH and elevated temperature. Internalization by cells in culture (HeLa, MDCK) was rapid and in the same range as for virus and virosomes (Bron et al., Biochemistry 33: 9110-9117, 1994; Nunes-Correia et al., Biochemistry 38: 1095-1101, 1999).

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

EXAMPLES

Example 1

Materials and Methods: Chemicals: Octaethyleneglycol-mono-(n-dodecyl)ether (OEG, $C_{12}E_8$) and didodecyldimethylammonium bromide (DDAB) were from Fluka, poly-L-lysine hydrobromide (MW 29'300), protamine sulfate, -cellulose, microcrystalline cellulose and 1,2-Dipalmitoyl-sn-glycero-3-phospho-rac-(1-glycerol) (PG) were purchased from Sigma (Buchs, Switzerland). Egg phosphatidyl choline (PC) was obtained from Lipoid (Cham, Switzerland).

Phosphatidylethanolamine (PE) was obtained from R. Berchtold (Biochemical Laboratory, University of Bern, Switzerland). Bio-beads SM2 and Bio-Gel A-15m were from Bio-Rad Laboratories (Glattbrugg, Switzerland). POPC, N-NBD-PE and N-Rh-PE were from Avanti Polar Lipids (Birmingham, Ala., USA). Pancreatic DNase I (from bovine pancreas) with a specific activity of 2000 Kunitz units/mg and exonuclease III (E. coli with 100 units/μl) were purchased from Roche Diagnostics (Basel, Switzerland) and New England BioLabs (BioConcept, Allschwil, Switzerland). Taq DNA polymerase was from Promega (Catalys, Wallisellen, Switzerland). N-(4,4-difluoro-5,7-diphenyl-4-bora-3a,4a-diaza-s-indacene-3-propionyl)-1,2-dihexadecanoyl-sn-glycero-3-phosphoethanolamine (Bodipy 530/550-DHPE), ethidium monoazide bromide (EMA), Texas red-dextran (MW 70'000) and PicoGreen reagent were from Molecular Probes Europe (Leiden, The Netherlands). The oligonucleotides used for the polymerase chain reaction and for the antisense experiments were from Microsynth (Balgach, Switzerland). The plasmids pT7-EGFP, VRO112, EGFP-VRO112 and $^{35}$S-labelled plasmid were a kind gift of Karin Moelling (Institute of Medical Virology, University of Zurich, Switzerland).

Viruses: Influenza viruses of the X-31 recombinant strain and the A/PR/8/34 (PR8) strain, propagated in the allantoic cavity of embryonated eggs (Gerhard, J. Exp. Med. 144: 985-995, 1976), were obtained from Bema Biotech (Bern, Switzerland). The recombinant vaccinia virus vTF7-3 was a kind gift of Karin Moelling (Institute of Medical Virology, University of Zurich, Switzerland).

Cell culture: MDCK and HeLa cells were maintained in MEM (Life Technologies, Basel, Switzerland) supplemented with 10% FCS, penicillin (100 IU/ml) and streptomycin (100 μg/ml).

Example 2

Preparation of immunopotentiating reconstituted influenza virosomes (IRIV): Virosomes were prepared by the method described by Bron and coworkers (Bron et al., Methods Enzymol. 220: 313-331, 1993). Briefly, virus (1.5 μmol of phospholipid or 5 mg of viral protein) was sedimented by ultracentrifugation and solubilized in 0.7 ml of 100 mM OEG in phosphate-buffered saline (PBS, 150 mM NaCl, 5 mM Na-phosphate, pH 7.4). The nucleocapsid was removed by ultracentrifugation (100'000×g, 30 min). The supernatant (containing the viral lipids and the envelope proteins) was shaken (1200 rpm) with 180 mg of wet Bio-Beads SM2 for 1 h at room temperature and twice for 10 min with 90 mg of Bio-Beads at 1400 rpm to remove the detergent.

Subsequently, the virosome preparation was centrifuged on a 10-40% (w/v) discontinuous sucrose density gradient in PBS at 130'000×g for 90 min. The virosomes were collected from the interface between the sucrose layers.

Chimeric virosomes containing HAs from X-31 and PR8 were prepared similarly. Equal amounts of viral proteins from the two virus strains were mixed before solubilization.

The hemagglutinin/phospholipid ratio was determined by phospholipid determination after Bottcher (Bottcher et al., Anal. Chim. Acta 24: 202-203, 1961) and HA-quantification after SDS-PAGE with the Coomassie-extraction method after Ball (Ball, Anal. Biochem. 155: 23-27, 1986).

Example 3

Preparation of conventional IRIV with encapsulated molecules: IRIV were basically prepared as described by Zurbriggen et al. (Zurbriggen et al., Prog. Lipid Res. 39:3-18, 2000). Briefly, 32 mg egg PC and 8 mg PE were dissolved in 2 ml of PBS containing 100 mM OEG (PBS/OEG). Influenza A/Singapore was purified as described (Skehel and Schild, Virology 44:396-408, 1971). Influenza virus corresponding to 4 mg hemagluttinin (HA) was centrifuged at 100,000×g for 30 min and the pellet was dissolved in 1 ml of PBS/OEG. To prepare peptide-IRIV, 4 mg of peptide was dissolved in 1 ml PBS/OEG. The phospholipids, the dissolved virus solution and the peptide solution were mixed and sonicated for 1 min. This mixture was centrifuged at 100,000×g for 1 h and the supernatant sterile filtered (0.22 µm). Virosomes were then formed by detergent removal using 180 mg of wet SM2 Bio-Beads for 1 h at room temperature with shaking and three times for 30 min with 90 mg of SM2 Bio-Beads. Size determination of IRIV was done by light scattering using a Zetasizer 1000HS instrument (Malvern Instruments, UK). For quantification of encapsulated peptide, a fraction of the homogenous IRIV were loaded on a Sephadex G50 Coarse (Amersham Biosciences, Switzerland) gel-filtration column and separated from non-encapsulated peptide. Peptide quantification was done on an Äkta Explorer 10 (Amersham Biosciences, Switzerland) using a CC 125/4.6 Nucleosil 100-5 C8 reverse-phase column (Macherey-Nagel, Switzerland).

To prepare protein-IRIV (e.g. GFP-IRIV), 10 µg of protein was dissolved in 1 ml PBS/OEG and continued as described above. To prepare PicoGreen-IRIV, 20 µl of the stock solution was dissolved in 1 ml PBS/OEG and continued as described above. GFP and PicoGreen quantification were done on a LS 55 Luminescence spectrometer (Perkin Elmer Instruments, USA).

Chimeric virosomes containing HAs from Influenza X-31 and Influenza A/Singapore were prepared similarly, but the peptide solution was replaced by 1 ml of OEG/PBS. Equal amounts of HA protein from the two virus strains were mixed before solubilization.

Example 4

Preparation of large unilamellar vesicles (LUVs): Twelve milligrams of POPC/DDAB (98:2, molar ratio) were dissolved in chloroform/methanol. Subsequently, the solvent was removed by evaporation, followed by an overnight drying at 10-2 mm Hg. The dried lipid mixture was dispersed in 50 µl Tris buffer (50 mM Tris, pH 8.0) and sonicated for 15 min in a bath sonicator. Following addition of the substance to be encapsulated the concentration of lipids was adjusted to 120-160 mM. The dispersion was frozen in liquid nitrogen and thawed at room temperature ten times. Before extrusion, the liposome dispersion was diluted with Tris buffer to a lipid concentration of 40 mM and extruded ten times each through 0.2 µm and 0.1 µm polycarbonate membranes (Nucleopore Track-Etch Membrane, Sterico, Switzerland) with a home made extruder (similar to the LiposoFast from Avestin Inc.).

Plasmid DNA was, in principle, encapsulated as described by Monnard and co-workers (Monnard et al., Biochim. Biophys. Acta 1329: 39-50, 1997). To the sonicated liposomes 10 µg of DNA (for some experiments containing also $^{35}$S-labeled plasmid-DNA) were added and treated as described above. Non-entrapped DNA was digested by adding 700-800 units of pancreatic DNase I, 200 units of exonuclease III, 5 mM $MgCl_2$ and 0.1 mM DTT to the DNA-containing liposomes (for experiments with higher quantities of DNA the amount of enzymes was proportionally adjusted). After incubating for 3 h at 37° C., the reaction was stopped by adding EDTA to final concentration of 7 mM. The external bulk medium was separated from the liposomes by gel filtration spin column chromatography (Bio-Gel A-15m, previously equilibrated with Tris-HCl buffer, pH 8.0). Usually, the columns were centrifuged at 165×g for 2 min. Ten to fifteen fractions of about 50 µl each were collected. The fractions 2-7 were usually turbid, (the others showed no visible turbidity, indicating that they contained no significant amount of liposomes).

Quantification of entrapped DNA into LUVs: To determine the fraction of entrapped plasmid-DNA, $^{35}$S-labeled DNA was co-entrapped into liposomes. From the amount of radioactivity initially added and the quantity of radioactivity still associated with liposomes after extensive DNase I/exonuclease III digestion and gel filtration chromatography, the proportion of entrapped DNA could be determined by liquid scintillation counting.

Quantification was also performed by visualization of the plasmid-DNA on 1% agarose gels before and after digestion. For these experiments plasmid-DNA of untreated liposomes or of liposomes that were DNase I/exonuclease III digested and gel filtration purified was phenol/chloroform extracted. The aqueous solution containing the DNA was subjected to gel electrophoresis. The gel was stained with ethidium bromide and the bands corresponding to plasmid-DNA quantified visually on the basis of known amounts of plasmid.

Example 5

Preparation of large unilamellar vesicles (LUVs): 36.4 µmol (27.95 mg) PC and 15.6 µmol (10.75 mg) PG (molar ratio 70:30) were dissolved in methanol/chloroform (2:1). The solvent was removed by using a rotary evaporator (Rotavapor R-205, Büchi Labortechnik, Switzerland) at 40° C. at a gradual vacuum of 30-10 kPa. For peptide-liposomes with hydrophobic peptides, 2-3.5 mg peptid was dissolved in methanol and added to the phospholipid mixture before solvent removal. The dried lipid film was hydrated with 500 µl PBS. For peptide-liposomes with hydrophilic peptides, the dried lipid film was hydrated with 350 µl PBS containing 2-3.5 mg peptide to be encapsulated. For GFP-liposomes, the dried lipid film was hydrated with 350 µl PBS containing 10 µg GFP. For PicoGreen-liposomes, the dried lipid film was hydrated with 350 µl PBS containing 1.75 µl PicoGreen stock solution. Before extrusion, the volume was adjusted to 500 µl with PBS. The liposome dispersion was extruded ten times through polycarbonate membranes (Nucleopore Track-Etch membrane, 0.1 µm or 0.2 µm, respectively, Whatman, UK) with a 1.5 ml Lipex Extruder (Northern Lipids, Canada). Size determination of extruded liposomes was done by light scattering using a Zetasizer 1000HS instrument (Malvern Instruments, UK). For quantification of encapsulated peptide, a fraction of the homogenous liposomes were loaded on a Sephadex G50 Coarse (Amersham Biosciences, Switzerland) gel-filtration column and separated from non-encapsulated peptide. Peptide quantification was done on an Äkta Explorer 10 (Amersham Biosciences, Switzerland) using a CC 125/4.6 Nucleosil 100-5 C8 reverse-phase column (Macherey-Nagel, Switzerland). GFP and PicoGreen quantification were done on a LS 55 Luminescence spectrometer (Perkin Elmer Instruments, USA).

Example 6

Preparation of chimeric proteoliposomes: Chimeric virosomes (50 µl) were incubated with 2 µl of POPC/DDAB LUVs at 4° C. in PBS (final volume 200 µl) adjusted to pH 5.0 with 5 µl of citric acid (150 mM, adjusted to pH 3.5). After neutralization with 1.4 µl of 1 M NaOH, fusion products were extruded ten times through 0.2 µm polycarbonate membranes. Fused proteoliposomes were prepared freshly for each experiment, since it was noted that they are prone to aggregation.

In order to analyze whether extrusion leads to loss of DNA, liposomes containing $^{35}$S-labeled DNA were fused with chimeric virosomes and extruded as described above. Proteoliposomes were then digested with DNase I and Exonuclease III as already described above. The fraction of radioactivity associated with proteoliposomes after gel filtration chromatography was determined by liquid scintillation counting. Control probes were treated the same except that they were either not extruded or extruded but not digested.

Fusion measurements by FRET: For in vitro fusion experiments 0.6% each of N-NBD-PE and N-Rh-PE were incorporated into LUVs consisting of POPC/DDAB (98:2) (1 mg/ml). Fluorescence measurements were carried out at 4° C. and 37° C. in a final volume of 2 ml PBS (5 mM Na-phosphate, pH 7.4 and 150 mM NaCl). Liposomes (19 µl) and 30-50 µl of virosomes were present in the cuvette. After addition of 48 µl of citric acid (150 mM, adjusted to pH 3.5 with NaOH) an increase in fluorescence was recorded continuously at excitation and emission wavelengths of 465 nm and 530 nm, respectively. Measurements were carried out with a SPEX Fluorolog-2 fluorometer (SPEX Industries, Edison, N.J., USA) equipped with a thermostated cuvette holder and a magnetic stirring device. For calibration of the fluorescence scale the initial residual fluorescence of the liposomes was set to zero and the fluorescence at infinite probe dilution determined after the addition of Triton X-100 (0.5% v/v final conc.) to 100%.

Cryo transmission electron microscopy (Cryo-TEM): Small drops of a virosome- or liposome-containing dispersion were applied to carbon-coated copper grids and frozen immediately in liquid ethane in a controlled environment vitrification system (Egelhaaf et al., J. Microsc. 200: 128-139, 2000). Vitrified specimens were transferred using a modified cryoholder (Gatan, Pleasanton, Calif., USA) into a transmission electron microscope (Zeiss EM 912 OMEGA) operated at 120 keV and 'zero loss' conditions. After an equilibration time of 5 min the specimens were examined at −170° C. Electron micrographs were digitally recorded without flat field correction using a cooled 1024×1024 CCD camera (Proscan, Germering, Germany) controlled by a SYS image analysis system version 2.1 (SYS, Münster, Germany).

Example 7

Preparation of chimeric proteoliposomes: Chimeric virosomes (600 µl in PBS) were incubated with 200 µl of PC/PG LUVs at 15° C. in PBS under constant stirring. To trigger the fusion the pH was adjusted to about 4.5 with 15 µl of 1 M HCl. After incubation for 30 min, the mixture was neutralized with 15 µl of 1 M NaOH and fusion products were extruded ten times through 0.2 µm polycarbonate membranes as described in example 4. For in vitro fusion measurements by FRET, an alternative assay was developped: 0.75 mol % of Bodipy530/550-DHPE and 0.25 mol % of Rh-DHPE were incorporated into LUVs consisting of PC/PG (70:30). Bodipy530/550-DHPE is advantageous over N-NBD-PE since its extinction coefficient is three times higher and less sensitive to the solvent. Fluorescence measurements were carried out at distinct temperatures between 4° C. and 42° C. in 5 mM sodium phosphate buffer pH 7.5, 100 mM NaCl, in a final volume of 0.8 ml in 2.5 ml PMMA micro-cuvettes (VWR, Switzerland) under continous stirring. Typically, 1 µl of labeled liposomes (0.3 µmol phospholipid) were mixed with 5-50 µl of virosomes and fusion was triggered by addition of 3.75-7 µl of 1 M HCl, resulting in a pH around 4.5. The increase in fluorescence was recorded continuously at excitation and emission wavelengths of 530 nm and 550 µm, respectively, with an excitation slit of 2.5 nm and an emission slit of 15.0 nm. Measurements were carried out with a LS 55 Luminescence spectrometer (Perkin Elmer Instruments, USA) equipped with a thermostated cuvette holder and a magnetic stirring device. The maximal fluorescence at infinite probe dilution was reached after addition of Triton X-100 (0.5% v/v final concentration).

Example 8

Transfection experiments: MDCK or HeLa cells (1×10$^5$) were seeded on 24 well plates the day before transfection and transfected with 1 µg of plasmid DNA (EGFP-VR1012) per well, using SuperFect reagent according to the manufacturer's protocol (Qiagen, Basel, Switzerland).

Preparation of rhodamine-labeled chimeric proteoliposomes: One milligram of lipids (POPC/DDAB/N-Rh-PE 98:2:0.5) were dissolved in chloroform/methanol. Subsequently the solvent was removed by evaporation followed by overnight drying at 10-2 mm Hg. The dried lipids were dispersed in 200 µl PBS. The dispersion was frozen in liquid nitrogen and thawed at room temperature ten times. After that, liposomes were extruded ten times through each 0.2 µm and 0.1 µm polycarbonate membranes.

Rhodamine-labeled proteoliposomes were prepared from 50 µl of rhodamine-LUVs and 100 µl of chimeric virosomes in a total volume of 200 µl as described above. Briefly, the dispersion was acidified and incubated for 10 min at 4° C. Following neutralisation with 1 M NaOH, proteoliposomes were extruded ten times through a 0.2 µm polycarbonate membrane.

For transfection with DNA-containing proteoliposomes the same number of cells was seeded. Chimeric proteoliposomes (10-20 µl) containing the EGFP-VR1012 plasmid were incubated with the cells in 200 µl medium (MEM or MEM supplemented with 10% FCS, or RPMI containing 0.2% BSA) at 4° C. for 1 h or at 37° C. for 2.5-4 h before removing the medium. The cells were then incubated in total growth medium at 5% CO$_2$ and 37° C. for 48-70 h.

Transfected cells were examined for EGFP expression using a Zeiss Axiovert wide-field microscope.

Example 9

Cellular uptake studies of rhodamine-labeled proteoliposomes: MDCK or HeLa cells ($1 \times 10^5$) were grown to 60-80% confluency on 12 mm Alcian blue-coated coverslips and incubated with 10 µl of rhodamine-labeled proteoliposomes in 100 µl RPMI-medium supplemented with 20 mM HEPES and 0.2% BSA for 1 h at 4° C. protected from light. Cells were then washed extensively with ice-cold PBS and incubated in total growth medium (MEM, 10% FCS) at 5% $CO_2$ and 37° C. At the indicated time points, cells were fixed with 3.7% (v/v) formaldehyde. Coverslips were mounted in Moviol and examined using a Zeiss Axiovert wide-field microscope. Images were collected using a CCD camera (Hamamatsu) and standard filters.

Cellular localization studies of ethidium monoazide bromide(EMA)-labeled DNA: EMA-labeled plasmid DNA was essentially prepared as described (Zabner et al., J. Biol. Chem. 270: 18997-19007, 1995; Serikawa et al., Biochim. Biophys. Acta 1467: 419-430, 2000). To 200 µg EGFP-VR1012 in 100 µl of $H_2O$ were added 5 µg of EMA (5 mg/ml in EtOH). After a 15 min incubation period on ice, the solution was photoactivated (SUSS LH 1000 lamphouse (KARL SUSS, Waterbury Center, Vt., USA) equipped with an OSRAM HBO 350 W high pressure mercury lamp) for 10 min. To remove free reagent, the DNA was precipitated three times with 3 volumes of ethanol and 0.1 volumes of 3 M sodium acetate (pH 5.2). Labeled DNA was resuspended in 70-100 µl of $H_2O$.

EMA-labeled DNA was then either encapsulated into LUVs and used for transfection experiments with proteoliposomes or prepared with SuperFect as described above. For intracellular localization studies of EMA-labeled DNA a Zeiss Axiovert wide-field microscope was used.

Cellular uptake studies of proteoliposomes containing Texas red-dextran: To 6 mg of dried lipids (POPC/DDAB 98:2) in 50 µl Tris-HCl buffer (50 mM Tris-HCl, pH 8.0) were added 3 mg of Texas red-dextran (70'000 MW) in 30 µl Tris buffer. Liposomes were prepared as described above. Free dextran was separated from liposomes by a sucrose density gradient. Briefly, 100 µl of the extruded liposomes were mixed with 900 µl of 60% sucrose in Tris-HCl buffer, then 1 ml each of 30%, 20% and 10% sucrose were layered on top. The final layer consisted of 500 µl Tris-HCl buffer. Gradients were centrifuged for 3 h at 35'000 rpm and 20° C. in a SW 55 Rotor (Beckman). Dextran-containing liposomes could be collected as a fine band in the upper regions of the gradient. The collected fraction was diluted with Tris buffer and concentrated to ca. 200 µl with an ultrafree centrifugal filter device (Millipore, Volketswil, Switzerland).

Texas red-dextran-containing liposomes were fused with chimeric virosomes in the cold as described above. The fusion products were incubated with cells as already described. Uptake and release of Texas red-dextran into the cytosol was analyzed by fluorescence microscopy with a Zeiss Axiovert wide-field microscope after fixation of cells.

Example 10

Transfection experiments using the T7-cytoplasmic expression system: HeLa cells ($3 \times 10^5$) grown on coverslips were infected with vTF7-3 (MOI of 5). After 1 h the incubation medium was removed, and the cells were transfected with proteoliposomes containing pT7-EGFP or with lipofectamin according to the manufacturer's protocol (Invitrogen AG, Basel, Switzerland). The medium was replaced 4 h after transfection, and the cells were incubated for an additional 40-60 h before analysis for GFP expression by fluorescence microscopy.

Plasmid isolation from transfected cells and amplification by polymerase chain reaction: MDCK and HeLa cells were grown to 60-80% confluency on 60 mm plates. EGFP-VR1012 encapsulated in proteoliposomes or as Superfect-complexes was added to cells as described. After different incubation times at 37° C. cells were lysed and plasmid isolated by Hirt extraction (Hirt, J. Mol. Biol. 26: 365-369, 1967). Briefly, 0.4 ml of a 0.6% (w/v) SDS, 10 mM EDTA solution were added to each plate, and incubated for 20 min at room temperature. Cells were scraped off with a rubber policeman. The viscous mixture was pipetted into an Eppendorf tube, 100 µl of a 5 M NaCl solution were added, and the mixture was chilled on ice for at least 5 h. After centrifuging for 4 min at 14'000 rpm at 4° C., the supernatant was carefully removed and extracted twice with phenol and once with chloroform. The aqueous phase was precipitated with 3 volumes of ethanol and 0.1 volumes of 3 M sodium acetate (pH 5.2) overnight at −20° C. The pellet was washed with 70% ethanol and resuspended in 20 µl of $H_2O$.

For the polymerase chain reaction (PCR) the following reagents were assembled in a total volume of 20 µl:

1-2 µl isolated plasmid DNA
1× Taq DNA polymerase buffer
1.5-2 mM $MgCl_2$
20 µM dNTPs (5 µM each)
1 µM of each primer
1 U Taq DNA polymerase The primers used were:

```
VR1012-for:
5'-GCCACCAGACATAATAGCTG-3'    (SEQ ID NO:1)

EGFP-rev:
5'-GGCTGTTGTAGTTGTACTCC-3'    (SEQ ID NO:2)
```

Cycling parameters:

| | |
|---|---|
| 1 cycle | 94° C. 45 s |
| 19-24 cycles | 94° C. 45 s |
| | 52° C. 45 s |
| | 72° C. 45 s |
| 1 cycle | 72° C. 10 min |

The products were then analyzed on a 8% (v/v) polyacrylamide gel with a thickness of 1 mm.

Gel protocol:

1 ml 40% (v/v) acrylamide
1 ml 5× TBE
2.625 ml $H_2O$
375 µl Glycerol
30 µl 10% (w/v) APS
6 µl TEMED Condensation of DNA with poly-L-lysine or protamine-sulfate: DNA-poly-lysine/DNA-protamine complexes were prepared by the slow addition of varying amounts of polycation (12.5-100 µg) to 50 µg of plasmid DNA and 2.5 µmol of lipids (POPC/DDAB 98:2) in total 0.5 ml of $H_2O$ or PBS.

Example 11

Antisense-Experiments: Preparation of proteoliposomes containing c-myc oligodeoxynucleotides: One hundred microliters of a 15 mM c-myc oligodeoxynucleotide-stock solution (final 1.5 µmol) were added to the sonicated lipid dispersion and treated as described for the preparation of LUVs. Not encapsulated oligodeoxynucleotides were removed by gel filtration as described for encapsulation of plasmid DNA (without digestion). The first four eluates containing liposomes were pooled and concentrated with an ultrafree centrifugal filter device (Millipore, Volketswil, Switzerland) to the original volume (50 µl).

Sequences of oligodeoxynucleotides (phosphorothioated) used:

```
antisense:  5'-AACGTTGAGGGGCAT-3'   (SEQ ID NO:3)

scrambled:  5'-GAACGGAGACGGTTT-3'   (SEQ ID NO:4)
```

Oligodeoxynucleotides-containing LUVs were fused with chimeric virosomes and subsequently extruded.

Encapsulation of c-myc oligodeoxynucleotides into PR8-virosomes: To encapsulate c-myc oligodeoxynucleotides directly into PR8-virosomes, 1.5 µmol oligodeoxynucleotides in 100 µl of $H_2O$ were added to the solubilized viral fraction. PR8-virosomes were then prepared as described above.

Cellular delivery of oligodeoxynyncleotides: HeLa cells ($4-6\times10^3$ per well) were seeded the day before transfection in a 96 well plate. For transfections with oligofectamine (Invitrogen AG, Basel, Switzerland) cells were kept in growing medium without penicillin/streptomycin. Cells were treated with c-myc antisense and scrambled phosphorothioated oligonucleotides complexed with oligofectamine according to the manufacturer's protocol.

For transfections with ODN-containing proteoliposomes 2-3 µl of fused virosomes were incubated with cells in total 100 µl of medium (RPMI with 0.2% BSA or MEM or MEM with 10% FCS) at 37° C. and 5% $CO_2$ for three days. For some experiments proteoliposomes were first incubated at 4° C. for 1 h. Unbound particles were washed away, growing medium was added and incubated at 37° C. as described. Cell proliferation was tested after 70 h with the "CellTiter 96AQueous one Solution Cell Proliferation Assay" as described by the manufacturer (Promega (Catalys, Switzerland). After addition of 20 µl of reagent per well and a 1 to 3 hours-incubation at 37° C. and 5% $CO_2$, absorbance was recorded at 450 nm using a Benchmark microplate reader (Bio-Rad Laboratories, Glattbrugg, Switzerland).

Cellular uptake studies of FITC-labeled oligodeoxynucleotides: HeLa cells ($1\times10^5$) seeded on 12 mm coverslips were treated with oligofectamin and FITC-labeled oligodeoxynucleotides as described above.

The same number of cells was seeded for treatment with chimeric proteoliposomes or PR8-virosomes. 20 µl of proteoliposomes or 10 µl of PR8-virosomes containing FITC-labeled oligodeoxynucleotides were incubated with cells in 200 µl of medium (RPMI containing 0.2% BSA) at 4° C. for 1 h. Medium was then removed and cells were incubated in total growth medium at 5% $CO_2$ and 37° C.

At the indicated time points cells were fixed with 3.7% (v/v) formaldehyde. Coverslips were mounted in Moviol and examined using a Zeiss Axiovert wide-field microscope. Images were collected using a CCD camera (Hamamatsu) and a standard FITC-filter.

Example 12

Fusion experiments with erythrocytes: Freshly washed chicken erythrocytes (0.8%) were received from Berna Biotech (Bern, Switzerland) in $PBS^+$ (7 mM $Na_2HPO_4$, 5 mM $KH_2PO_4$, 138 mM NaCl, 3 mM KCl and 1 mM $MgCl_2$, pH 7.2).

Before each experiment, erythrocytes were centrifuged for 5 min at 830×g and resuspended in PBS (150 mM NaCl, 5 mM Na-phosphate, pH 7.4) or in $ddH_2O$ to the same volume (500 µl). Different amounts of virus (1-20 µg protein) and corresponding amounts of virosomes (PR8, X-31), chimeric virosomes and proteoliposomes were added and incubated for 15 min at 37° C. under gentle shaking at pH 5.0, pH 5.5, pH 6.0 and pH 7.3, respectively. Subsequently the samples were neutralized with 1 M NaOH. Erythrocytes were sedimented for 5 min at 830×g. The absorbance of the supernatant was measured at 541 nm to determine the hemolytic activity. The percentage hemolysis was measured by $100\times(A-A_0)/(A_{100}-A_0)$, where $A_{100}$ was the absorbance for 100% hemolysis determined for erythrocytes in distilled water and $A_0$ was the base line absorbance measured in the absence of virus/virosomes.

The cell pellet was resuspended in 500 µl PBS. Drops of the suspension were added to a coverslip and prepared for light microscopy.

To inactivate chimeric virosomes, 50 µl of virosomes were incubated in a total volume of 200 µl at 37° C. Following acidification with 5 µl of citric acid (150 mM, pH 3.5), the suspension was incubated for another 30 min at 37° C. and reneutralized with 1.4 µl of 1 M NaOH. Twenty microliter of this mixture were used per hemolysis reaction.

Photolabeling experiments: Biotinyl-TID-PE/16 containing PR8-virosomes were prepared as described above, with the exception that after the solubilization step with $C_{12}E_8$ 300 nmols (10% of the viral phospholipids) of dried biotinyl-TID-PE/16 were added.

For the preparation of biotinyl-TID-PE/16 containing proteoliposomes LUVs prepared from POPC/DDAB/biotinyl-TID-PE/16 (98:2:20) (5 mg/ml) were fused with chimeric virosomes. Biotinyl-TID-PE/16-LUVs (20 1) were incubated with 50 1 of chimeric virosomes in a total volume of 200 1 at pH 5.0 and 4° C. for 10 min. Subsequently, the mixture was neutralized and proteoliposomes extruded ten times through 200 nm pores.

Preparation of ghosts from human erythrocytes: Fresh human blood was obtained from the Stiftung Zurcher Blutspendedienst (SRK), Blutspendezentrum Zurich (Switzerland). In order to isolate red blood cells 20 ml of blood were filtered through a bed of -cellulose and microcrystalline cellulose (1 g each) in PBS (138 mM NaCl, 10 mM Na-phosphate, pH 7.3) as previously described by Beutler (Beutler et al., J. Lab. Clin. Med. 88: 328-333, 1976). The filtrate was washed 4 times by sedimenting cells in a SS-34 rotor (Sorvall) at 2500 rpm and 4° C. for 7 minutes and resuspending the cells in PBS. After the final wash cells were resuspended in 20 ml PBS and prepared (as described by the manufacturer) for counting on a Sysmex Microcellcounter F-800 (TOA Medical Electronics, Inc., Hamburg, Germany).

Ghosts were essentially prepared as described by Steck (Steck and Kant, Methods Enzymol. 31: 172-180,1974).

Packed erythrocytes (1 ml) were mixed with 40 ml of hemolysis buffer (5 mM phosphate, pH 7.4, 1 mM EDTA, 15 µg/ml PMSF). Ghosts were pelleted by centrifugation at 22'000×g for 10 min. The supernatant and a small, hard button, rich in contaminating proteases, were carefully aspirated. Membranes were resuspended in hemolysis buffer and washed three more times until they were creamy white. Finally, ghosts were resuspended in 1 ml of hemolysis buffer.

Photolabeling experiments: Biotinyl-TID-PE/16 containing PR8-virosomes were prepared as described previously, with the exception that after the solubilization step with $C_{12}E_8$ 300 nmols (10% of the viral phospholipids) of dried biotinyl-TID-PE/16 were added. For the preparation of biotinyl-TID-PE/16 containing proteoliposomes LUVs prepared from POPC/DDAB/biotinyl-TID-PE/16 (98:2:20) (5 mg/ml) were fused with chimeric virosomes. Biotinyl-TID-PE/16-LUVs (20 µl) were incubated in 50 µl of chimeric virosomes in a total volume of 200 µl at pH 5.0 and 4 C for 10 min. Subsequently, the mixture was neutralized and proteoliposomes extruded ten times through 200 nm pores. Biotinyl-TID-PE/16-proteoliposomes (20 µl) or 5 µl of biotinyl-TID-PE/16-PR8-virosomes were incubated with 20 µl of ghosts in a total volume of 50 µl at 37° C. for 20 min. The low pH probes were incubated at the mentioned conditions after acidification with citrate buffer to pH 5.0. After reneutralization with 1 M NaOH, respective samples were photolysed for 90 s by placing them approx. 10 cm from a SUSS LH 1000 lamphouse (KARL SUSS, Waterbury Center, Vt.) equipped with an OSRAM HBO 350 Watt short-arc high pressure mercury lamp. Protein was precipitated with 3 volumes of chloroform/methanol 1:2 to remove unbound label. After that, samples were prepared for separation on a SDS 8% (v/v) polyacrylamide gel by electrophoresis.

Detection of biotinylated proteins was performed by western-blotting: Proteins separated by SDS-PAGE were transferred electrophoretically onto an Immobilon-P PVDF membrane (Millipore, Volketswil, Switzerland). The gel was blotted for 2 h at 110 mA in a transfer buffer containing 20% methanol, 20 mM Tris-HCl, 200 mM glycine. The blotting efficiency was checked by using the Kaleidoscope prestained protein standard (Bio-Rad Laboratories, Glattbrugg, Switzerland) and by staining the blotted gel with Coomassie blue.

The blot was blocked for a minimum of 1 hour with TBS-T (137 mM NaCl, 20 mM Tris-HCl, 0.1% (v/v) Tween 20, pH 7.6) containing 5% BSA at room temperature. The primary antibody (α biotin, Bethyl laboratories, Montgomery, Tex., USA) diluted 1:1000 in TBS-T containing 5% BSA was added and allowed to bind for 1 hour. The membrane was washed for 15 min with TBS-T, followed by two short (5 min) wash steps with TBS-T and one with TBS (137 mM NaCl, 20 mM Tris-HCl, pH 7.6). The second antibody (goat α-rabbit Horseradish peroxidase-conjugated, Pierce (Socochim, Lausanne, Switzerland)) diluted 1:20,000 in TBS-T containing 5% BSA was added and allowed to bind for 1 hour at room temperature. The membrane was again extensively washed as described above.

The wet blot was developed using the ECL$^+$Plus detection solution (Amersham Biosciences, Dubendorf, Switzerland) as described by the manufacturer.

Hemolysis and cell-cell fusion with human erythrocytes: Hemolysis and cell-cell fusion experiments with human erythrocytes were performed as described above for chicken erythrocytes. Per sample $6 \times 10^7$ washed red blood cells were used.

The invention claimed is:

1. A fusogenic vesicle encapsulating at least one therapeutic or immunologically active substance, said fusogenic vesicle comprising a first viral fusion protein, wherein the first viral fusion protein is X-31 hemagglutinin (HA) and at least one other viral fusion protein selected from the group consisting of influenza virus, VSV, SFV, Sendai virus, and HIV, wherein the at least one other viral fusion protein causes fusion at a different temperature than X-31 HA.

2. The fusogenic vesicle according to claim 1, wherein the vesicle is unilamellar.

3. The fusogenic vesicle according to claim 1 or 2, wherein the encapsulated therapeutic or immunologically active substance is selected from the group consisting of DNA, RNA, siRNA, proteins, peptides, amino acids and pharmaceutically active substances.

4. The fusogenic vesicle according to claim 3, wherein the encapsulated therapeutic or immunologically active substance is selected from the group consisting of a cosmetic agent, a pharmaceutical drug, an antigen or mixtures thereof.

5. The fusogenic vesicle according to claim 1, wherein at least one of the viral fusion proteins is cell type specific.

6. The fusogenic vesicle according to claim 1, wherein the at least one other viral fusion protein is from influenza virus.

7. The fusogenic vesicle according to claim 6, wherein the at least one other viral fusion protein is selected from the group consisting of PR8/34 and A/Singapore HA.

8. The fusogenic vesicle according to claim 1, further comprising lipids derived from the group consisting of glycolipids, phospholipids, cationic lipids, synthetic lipids and cholesterol.

9. The fusogenic vesicle according to claim 8, wherein the lipids comprise POPC and DDAB.

10. The fusogenic vesicle according to claim 1, further comprising lipids derived from a virus selected from the group consisting of influenza virus, VSV, SFV, Sendai virus and HIV.

11. The fusogenic vesicle according to claim 10, wherein the lipids are derived from influenza virus.

12. The fusogenic vesicle according to claim 1, wherein the vesicle has a diameter of between 100 and 300 nm.

13. The fusogenic vesicle according to claim 1, further comprising a cell-surface receptor, cytokine, growth-factor, antibody, or antibody fragment.

* * * * *